United States Patent
Wei

(10) Patent No.: US 10,195,217 B2
(45) Date of Patent: Feb. 5, 2019

(54) DI-ISOPROPYL-PHOSPHINOYL-ALKANES AS TOPICAL AGENTS FOR THE TREATMENT OF SENSORY DISCOMFORT

(71) Applicant: Edward T. Wei, Berkeley, CA (US)

(72) Inventor: Edward T. Wei, Berkeley, CA (US)

( * ) Notice: Subject to any disclaimer, the term of this patent is extended or adjusted under 35 U.S.C. 154(b) by 672 days.

(21) Appl. No.: 14/544,355

(22) Filed: Dec. 29, 2014

(65) Prior Publication Data

US 2015/0164924 A1    Jun. 18, 2015

(51) Int. Cl.
| | |
|---|---|
| *A61K 31/66* | (2006.01) |
| *A61K 9/00* | (2006.01) |
| *C07F 9/53* | (2006.01) |
| *A61K 49/00* | (2006.01) |

(52) U.S. Cl.
CPC ............ *A61K 31/66* (2013.01); *A61K 9/0014* (2013.01); *A61K 49/00* (2013.01); *C07F 9/532* (2013.01); *C07F 9/5304* (2013.01)

(58) Field of Classification Search
CPC ...... A61K 31/66; A61K 49/00; A61K 9/0014; C07F 9/5304
See application file for complete search history.

(56) References Cited

U.S. PATENT DOCUMENTS 4,070,496 A * 1/1978 Rowsell ................. A24B 15/30
131/276

\* cited by examiner

*Primary Examiner* — Bethany P Barham
*Assistant Examiner* — Peter Anthopolos

(57) ABSTRACT

The present discovery pertains generally to the field of therapeutic compounds. More specifically the present discovery pertains to certain di-isopropyl-phosphinoyl-alkanes as described herein, DIPA-1-5, DIPA-1-6, DIPA-1-7, DIPA-1-8, and DIPA-1-9, collectively referred to herein as "DIPA compounds", that are useful, for example, in the treatment of disorders (e.g., diseases) including: sensory discomfort (e.g., caused by irritation, itch, or pain); a skin dysesthesia; dermatitis; ocular pain and discomfort; heat discomfort; heat stress; flushing and/or night sweats (vasomotor symptoms); post-operative hypothermia; post-anaesthetic shivering; fatigue; tiredness; depression; cognitive dysfunction; and to enhance cognitive function. The applicant has found that localized delivery of DIPA compounds to the upper eyelid and/or facial skin has an alerting and enhancement effect on behavior and can be used to give a cosmetic refreshing look, to mental alertness, to reduce fatigue, and to improve work output. The present discovery also pertains to pharmaceutical compositions comprising such compounds, and the use of such compounds and compositions, for example, in therapy, in diagnosis of neuropathic pain, and in study of TRPM8 function.

3 Claims, 6 Drawing Sheets

*FIG. 4A* Wild Type

*FIG. 4B* Trp-M8 KO

DI-ISOPROPYL-PHOSPHINOYL-ALKANES AS TOPICAL AGENTS FOR THE TREATMENT OF SENSORY DISCOMFORT

CROSS-REFERENCE TO RELATED APPLICATIONS

This application is a continuation-in-part of International (PCT) Patent Application No PCT/GB2013/052750, filed Oct. 22, 2013.

BACKGROUND OF THE INVENTION

Field of the Invention

The present discovery pertains generally to the field of therapeutic compounds. More specifically the present discovery pertains to certain di-isopropyl-phosphinoyl-alkanes as described herein (DIPA-5, DIPA-1-6, DIPA-1-7, DIPA-1-8, and DIPA-1-9, collectively referred to herein as "DIPA compounds") that are useful, for example, in the treatment of disorders (e.g., diseases) including: sensory discomfort (e.g., caused by irritation, itch, or pain); a skin dysesthesia; atopic dermatitis; ocular pain and discomfort; heat discomfort; heat stress; flushing and/or night sweats (vasomotor symptoms); post-operative hypothermia; post-anaesthetic shivering; fatigue; tiredness; depression; cognitive dysfunction; and to enhance cognitive function. The present invention also pertains to pharmaceutical compositions comprising such compounds, and the use of such compounds and compositions, for example, in therapy, diagnosis, and laboratory investigations. The unusual property of the DIPA molecules is the ability to penetrate the keratinized layers of the skin [stratum corneum] to reach receptive targets underneath.

Description of Related Art

Heat abstraction from the body's surfaces can refresh the senses, relieve discomfort, attenuate pain, and suppress inflammation. Abstraction of heat from body surfaces evokes sensations that are termed cool, refreshing cool, chilly, cold, icy cold and painful cold. For example, air blown onto the face from a fan or an air-conditioner can reduce tiredness and increase alertness. A wet towel applied to the forehead can relieve discomfort from a fever or a headache. The methods of heat abstraction, with gas, liquids, or solids, achieve their effects by physically lowering tissue temperatures and by activating signals to the brain.

Chemical sensory/cooling agents are molecules that can mimic the sensations of heat abstraction without a change in tissue temperatures. The exact sensations produced by chemicals depend on the selection of the active ingredient and the site and method of delivery. With most of the agents currently in use, some degree of chemical cooling on the scalp and skin of the face, nostrils, and philtrum can be elicited, but the effects do not last long. For the skin of the torso and limbs overt sensations of coolness and cold are more difficult to elicit and sustain. The skin has a keratinized layer of dead cells, called the stratum corneum, that is a formidable barrier to drug penetration into the epidermis and dermis. The neuronal receptive fields to detect temperature changes are located in the skin sub-layers.

The term "chemical cooling agent" can be ambiguous because, for example, chemicals such as ethyl chloride as a gas, ethanol as a liquid, liquid nitrogen, or carbon dioxide as a solid, applied to the skin can evoke heat abstraction sensations by reducing tissue temperatures. In this application, chemical cooling agents will refer only to agents that elicit sensations of heat abstraction without a lowering of tissue temperatures.

The inventor has previously identified several p-menthane carboxamide compounds that, when applied to the philtrum skin, simulate effects of heat abstraction for >1.5 hr without decreasing tissue temperature (Wei, E T. Sensory/cooling agents for skin discomfort. Journal Skin Barrier Research 14: 5-12, 2012). These compounds are relatively water-insoluble.

"Thermal comfort" is a well-developed concept in ergonomics, engineering, and architecture. The term refers to a condition in which a person wearing a normal amount of clothing feels neither too cold nor too warm. Thermal comfort is important for one's well-being and for productivity. It is achieved when the air temperature, humidity, and air movement are within a specified range called the "comfort zone" [24 to 27° C. for UK and USA]. It is has been known for some time that an environmental temperature below 21.1° C. (70° F.) is optimal for work performance, and that the best temperature is in the range of 18.3 to 20° C. (65 to 68° F.) (Dawson et al., 2009, "Nine switches of human alertness", www.circadian.com, presentation from Circadian Technologies, Inc., Houston, Tex., USA, October 2009]. Experimentally, an improvement in performance can be demonstrated at 20° C. versus a 23° C. environment [Tham and Willem, Room air temperatures affects occupant's physiology, perceptions, and mental alertness. Building Environment 45: 40-44, 2010]. Conversely, careful studies have documented that work performance and productivity (output/input) drop by 2% for every increment of +1° C. above 25° C. up to 33° C. [Tanabe et al. Indoor environmental quality and productivity. Rehva Journal (Federation of the European Heating and Air Conditioning Associations) June, 2007]

The site where temperature is detected on the skin qualitatively affects perception of thermal comfort. Temperature sensitivity over the body surface varies over ~100 fold. The face, especially area around the eyes [periorbital] and mouth [perioral] are very sensitive, but the extremities have poor sensitivity, and the rest of the body is intermediate [Stevens et al. Temperature sensitivity of the body surface over the life span. Somatosensory Motor Research 15: 13-28, 1998]. The sensory innervation of the periorbital and perioral regions are mediated by the V1 and V2 branches of the trigeminal nerve [$5^{th}$ cranial nerve].

In hot conditions, humans prefer a cool face, and in cold they prefer a warm abdomen. The human brain is particularly susceptible to heat damage and can only tolerate ~40.5° C., while organs of the torso tolerate >42° C. Thus, a hot face would further heat an overheated brain, and preference for a low facial temperature in the heat has survival value [Nakamura et al. Relative importance of different surface regions for thermal comfort in humans. *Eur. J. Applied Physiology*, 113, 63-76, 2012]. Alleviating the sense of heat on the face can reduce discomfort and improve an organism's ongoing behavior. Facial cooling can also alert the organism and increase vigilance to focus on threats to its well-being. This fact is well-known to skiers and to people who live in countries with frigid winters.

Known Phosphine Oxides

The 1-dialkyl-phosphinoyl-alkanes [e.g. total number of carbons 16] are solvent-like molecules that require only several [1 to 3] steps for synthesis. They are also known as trialkylphosphine oxides, but the preferred term now is dialkyl-phosphinoyl-alkane [DAPA]. If two of the alkyl groups are isopropyl, the DAPA could be abbreviated as DIPA [diisopropyl-phosphinoyl-alkane], Rowsell and Spring [Phosphine oxides having a physiological cooling effect. U.S. Pat. No. 4,070,496. Jan. 24, 1978], describes a range of phosphine oxides which have a physiological cooling effect on skin and on the mucous membranes of the body, particularly the nose, mouth, throat and gastrointestinal tract. See, e.g., the table in columns 3 and 4 therein. Ten (10) of the compounds shown therein (Table 1) have one isopropyl group (shown as iso-$C_3H_7$). None of the compounds has two isopropyl groups.

TABLE 1

Compounds in Rowsell et al., 1978 P(=O)$R_1R_2R_3$

| # | $R_1$ | $R_2$ | $R_3$ |
|---|---|---|---|
| 2 | n-$C_7H_{15}$ | iso-$C_3H_7$ | sec-$C_4H_9$ |
| 3 | n-$C_8H_{17}$ | iso-$C_3H_7$ | sec-$C_4H_9$ |
| 7 | n-$C_6H_{13}$ | iso-$C_3H_7$ | sec-$C_4H_9$ |
| 8 | n-$C_6H_{13}$ | iso-$C_3H_7$ | cyclo-$C_5H_9$ |
| 11 | n-$C_7H_{15}$ | iso-$C_3H_7$ | cyclo-$C_5H_9$ |
| 12 | n-$C_6H_{13}$ | iso-$C_3H_7$ | iso-$C_5H_{11}$ |
| 15 | n-$C_7H_{15}$ | iso-$C_3H_7$ | iso-$C_5H_{11}$ |
| 26 | n-$C_6H_{13}$ | iso-$C_3H_7$ | n-$C_6H_{13}$ |
| 30 | n-$C_8H_{17}$ | iso-$C_3H_7$ | cyclo-$C_5H_9$ |
| 47 | iso-$C_3H_7$ | n-$C_4H_9$ | (n-$C_4H_9$)($C_2H_5$)CHCH$_2$ |

Wei, E. T. [Ophthalmic compositions and method for treating eye discomfort and pain. US 2005/0059639 A1, Mar. 17, 2005] describes the use of certain phosphine oxides and the treatment of eye discomfort by the administration of eye drops containing those compounds. See, e.g., Table 1 on page 4 therein. Five (5) of the compounds shown therein (Table 2) have one isopropyl group (shown as iso-$C_3H_7$).

TABLE 2

Compounds in Wei, 2005 P(=O)$R_1R_2R_3$

| # | $R_1$ | $R_2$ | $R_3$ |
|---|---|---|---|
| 14 | n-$C_6H_{14}$ | iso-$C_5H_{11}$ | iso-$C_3H_7$ |
| 15 | n-$C_7H_{15}$ | iso-$C_5H_{11}$ | iso-$C_3H_7$ |
| 17 | n-$C_6H_{14}$ | iso-$C_3H_7$ | sec-$C_4H_9$ |
| 18 | n-$C_7H_{15}$ | iso-$C_3H_7$ | sec-$C_4H_9$ |
| 19 | n-$C_8H_{17}$ | iso-$C_3H_7$ | sec-$C_4H_9$ |

Siddall et al. [Simplified preparation of some trisubstituted phosphine oxides. J. Chemical Engineering Data 10: 303-305, 1965] reported the synthesis of 1-di-isopropyl-octane [DIPA-1-8]. Unlike the Tables 1 and 2 compounds, the DIPA-1-8 compound has two isopropyl groups. No reports on any bioactivity of such di-isopropyl compounds have previously been made.

BRIEF SUMMARY OF THE INVENTION

Figure 1:
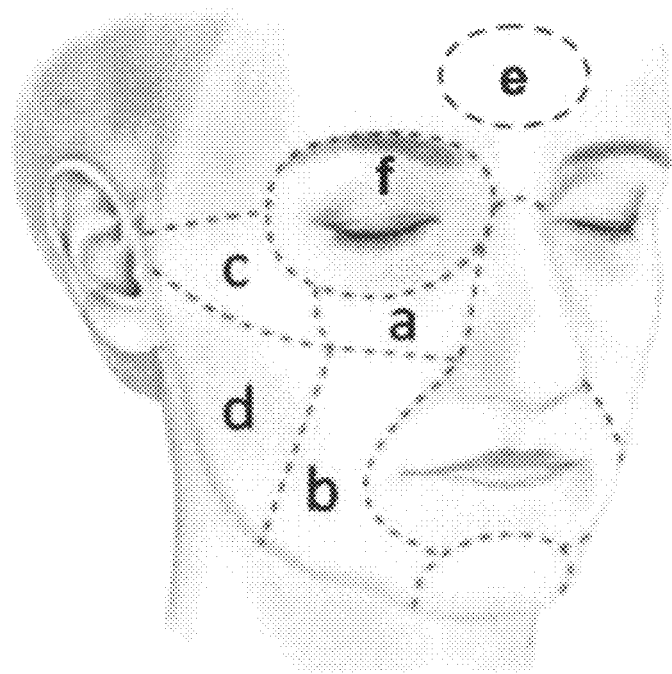
FIG. 1 is an illustration of a human head, showing facial sites for testing: (a) infraorbital, (b) buccal cheek, (c) zygomatic, (d) parotid-masseteric cheek, (e) frontal, and (f) periorbital. Sensations from the periorbital and frontal skin is transmitted via the ophthalmic branch of the trigeminal nerve [V1]. Diagram adapted from Pilsl et al. [Anatomy of the cheek: implications for soft tissue augmentation. Dermatologic surgery: official publication for American Society for Dermatologic Surgery 38, 1254-62, 2012].

In this discovery, it was found that application of a specific cooling agent to the periorbital area, especially to the skin of the eyelids, evoked a "dynamic cool" sensation that will arouse an organism and counteract tiredness. This change in mind-set is akin to a chemically-induced anti-fatigue agent such as caffeine. The subject becomes more alert and vigilant. The mode of drug delivery is that of a topical skin product, and not that of an ophthalmic product.

In another aspect of this discovery, a chemical has been created and identified as producing sensations of heat abstraction and penetrating keratinized tissues. The skin is a frequent site of injury. Inflammation is the response of tissues to injury and the cardinal signs of inflammation are a feeling of heat [calor] at the stie of injury, redness [rubor], swelling [tumor] and pain [dolor] in and around the injured tissues. The newly synthesized molecule may have value in the relief of the discomfort signs of irritation, itch, and pain from inflamed skin.

In another aspect of this discovery, the potent cooling agent synthesized that penetrates the skin to elicit cold [e.g., 1-di-isopropyl-phosphinoyl-heptane] may be used as a diagnostic tool to distinguish between pain of neuropathic versus somatic origin. Cold allodynia and hyperalgesia to cold are conditions frequently associated with neuropathic pain. In neuropathic pain application of a molecule of this discovery will be expected to exacerbate pain, but an opposite effect is expected in somatic pain. This differential action may be used diagnosis.

In another aspect of this discovery, the selective actions of the new molecules on TRPM8 were characterized. The current laboratory tools for the study of TRPM8 function are limited, and most investigators use menthol and icilin. The new molecules of this invention may be used as a set of more selective reagents for the study of the physiology and pharmacology of TRPM8 function.

One aspect of the invention pertains to certain di-isopropyl-phosphinoyl-alkanes described herein (collectively referred to herein as "DIPA compounds") and particularly compositions thereof and articles including such DIPA compounds such a pharmaceutical composition comprising one or more DIPA compound, as described herein, and a pharmaceutically acceptable carrier or diluent. Particularly preferred embodiments include one or more DIPA compounds and a delivery agent carrying the one or more compounds, where, the delivery agent is suitable for topical delivery Another aspect of the present discovery pertains to a DIPA compound, as described herein, for use in a method of treatment of the human or animal body by therapy, for example, for use a method of treatment of a disorder (e.g., a disease) as described herein.

Another aspect of the present discovery pertains to a kit comprising (a) a DIPA compound, as described herein, preferably provided as a pharmaceutical composition and in a suitable container and/or with suitable packaging; and (b) instructions for use, for example, written instructions on how to administer the compound.

DETAILED DESCRIPTION OF THE INVENTION

In this discovery, new water-soluble compounds [e.g., 1-di-isopropyl-phosphinoyl-heptane] have been identified that potently [<5 mg per dose] and rapidly produce on skin robust and intense cooling sensations. This type of drug action is unusual and has not been previously recognized to be achievable on keratinized surfaces and has lead to new applications as described herein.

Thus the present discovery relates to certain compounds (the DIPA compounds described herein) which, when delivered onto the skin, especially on periorbital facial skin, selectively and potently evoke sensations of "dynamic cool" for at least several hours. The dynamic cool can be repeated without significant diminution of the effects and can be sustained for the whole day. The sensations on the facial skin do not interfere with the individual's ability to fall asleep. The DIPA compounds may be used to counteract fatigue and enhance cognitive function. The DIPA compounds are administered topically, onto the eyelid skin and avoiding the cornea, and so effects are achieved without direct invasion of brain chemistry. The unusual, surprising feature of the DIPA compounds, relative to structurally similar analogs, is the ability to permeate through keratinized skin to produce strong sensations. This can be shown in laboratory animal experiments. Thus, these compounds also have applications in the treatment of skin discomfort, especially skin irritation, itch, and pain. The DIPA compounds may be used as selective laboratory reagents for the study of TRPM8 function, physiology, and pharmacology. In particular, the novel DIPA-1-7 embodiment may be used as a diagnostic agent to distinguish pain of neuropathic versus somatic origin.

DIPA Compounds

The compounds of the present discovery are examples of phosphine oxides, and more particularly, are examples of di-alkyl-phosphinoyl-alkanes [(O=)PR$_2$R$_2$R$_3$] wherein each of R$_1$, R$_2$, and R$_3$ is an alkyl group, and in particular where R$_1$ and R$_2$ are isopropyl, and R$_3$ is a linear alkyl group of 5 to 9 carbons and which have the following general formula of Formula 1:

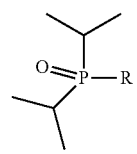

Formula 1 wherein R = n-pentyl, n-hexyl, n-heptyl, n-octyl, or n-nonyl

More specifically, the compounds of the present discovery are shown in Table 3 and collectively referred to herein as di(isopropyl)-phosphinoyl-alkanes [DIPA] or "DIPA compounds".

TABLE 3

DIPA-Compounds

| Code | Chemical Name | Formula/Weight | Chemical Structure |
|---|---|---|---|
| DIPA-1-5 | 1-di(isopropyl)-phosphinoyl-pentane | C$_{11}$H$_{25}$OP 204.32 | 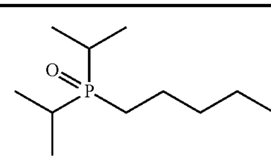 |
| DIPA-1-6 | 1-di(isopropyl)-phosphinoyl-hexane | C$_{12}$H$_{27}$OP 218.32 | 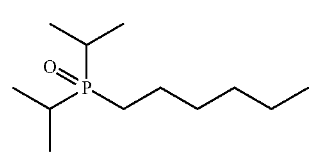 |

TABLE 3-continued

DIPA-Compounds

| Code | Chemical Name | Formula/Weight | Chemical Structure |
|---|---|---|---|
| DIPA-1-7 | 1-di(isopropyl)-phosphinoyl-heptane | $C_{13}H_{29}OP$ 232.34 | 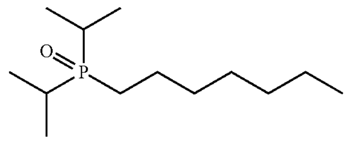 |
| DIPA-1-8 | 1-di(isopropyl) phosphinoyl-octane | $C_{14}H_{31}OP$ 246.37 | 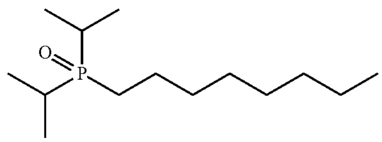 [SMILES: CCCCCCCCP(=O)(C(C)C)C(C)C] |
| DIPA-1-9 | 1-di(isopropyl) phosphinoyl-nonane | $C_{15}H_{33}OP$ 260.40 | 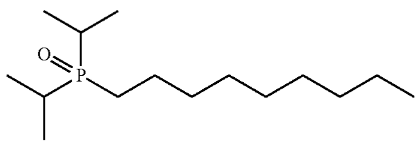 [SMILES: CCCCCCCCCP(=O)(C(C)C)C(C)C] |

Chemical Synthesis

The DIPA compounds were prepared by the following general method: 100 mL (23.7 g, ~200 mmol) of isopropylmagnesium chloride (or sec-butylmagnesium chloride in the case of the di-sec-butyl derivatives) were obtained from Acros, as a 25% solution in tetrahydrofuran (THF) and placed under nitrogen in a 500 mL flask (with a stir bar). Diethylphosphite solution in THF (from Aldrich, D99234; 8.25 g, 60.6 mmol in 50 mL) was added drop-wise. After approximately 30 minutes, the reaction mixture warmed up to boiling. The reaction mixture was stirred for an extra 30 minutes, followed by a drop-wise addition of the appropriate n-alkyl iodide solution in THF (from TCI; 60 mmol in 20 mL). The reactive mixture was then stirred overnight at room temperature. The reaction mixture was diluted with water, transferred to a separatory funnel, acidified with acetic acid (~10 mL), and extracted twice with ether. The ether layer was washed with water and evaporated (RotaVap Buchi, bath temperature 40° C.). The light brown oil was distilled under high vacuum. The final products, verified by mass as determined by mass spectrometry, were transparent liquids that were colourless or slightly pale yellow.

The following compounds were prepared by this method where Table 4A compounds are embodiments of the invention.

TABLE 4A

Chemical structures of tested compounds of this discovery.

| Code | Chemical Name | Chemical Structure |
|---|---|---|
| DIPA-1-5 | 1-di(isopropyl)-phosphinoyl-pentane | 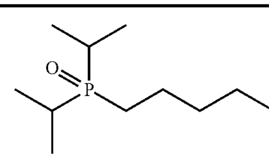 |
| DIPA-1-6 | 1-di(isopropyl)-phosphinoyl-hexane | 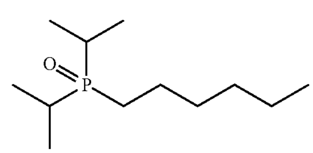 |
| DIPA-1-7 | 1-di(isopropyl)-phosphinoyl-heptane | 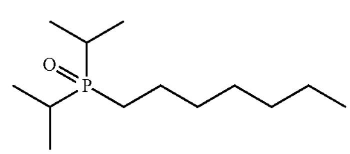 |

TABLE 4A-continued

Chemical structures of tested compounds of this discovery.

| Code | Chemical Name | Chemical Structure |
|---|---|---|
| DIPA-1-8 | 1-di(isopropyl)-phosphinoyl-octane | 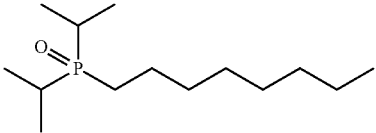 [SMILES: CCCCCCCCP(=O)(C(C)C)C(C)C] |
| DIPA-1-9 | 1-di(isopropyl)-phosphinoyl-nonane | 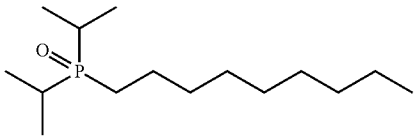 [SMILES: CCCCCCCCCP(=O)(C(C)C)C(C)C] |

TABLE 4B

Chemical structures of test compounds related to this discovery.

| Code | Chemical Name | Chemical Structure |
|---|---|---|
| 2-4 | 1-di(sec-butyl)-phosphinoyl-butane | 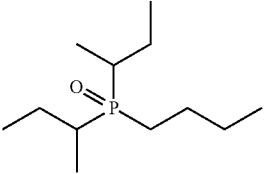 |
| 2-5 | 1-di(sec-butyl)-phosphinoyl-pentane | 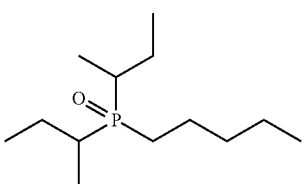 |
| 2-6 | 1-di(sec-butyl)-phosphinoyl-hexane | 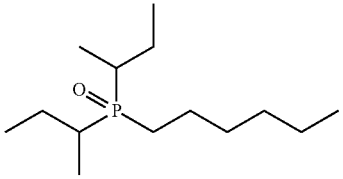 [SMILES: CCCCCCP(=O)(C(C)CC)C(C)CC] |
| 2-7 | 1-di(sec-butyl)-phosphinoyl-heptane | 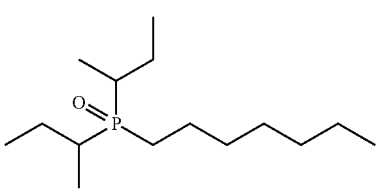 [SMILES: CCCCCCCP(=O)(C(C)CC)C(C)CC] |
| 2-8 | 1-di(sec-butyl)-phosphinoyl-octane | 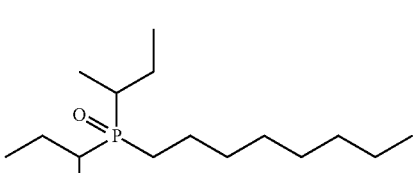 |

TABLE 4B-continued

Chemical structures of test compounds related to this discovery.

| Code | Chemical Name | Chemical Structure |
|---|---|---|
| 3-1 | 1-di(iso-butyl)-phosphinoyl-pentane | 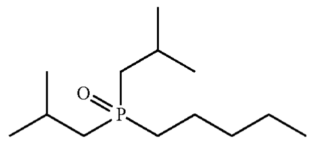 |
| 3-2 | 1-di(sec-butyl)-phosphinoyl-3-methyl-butane | 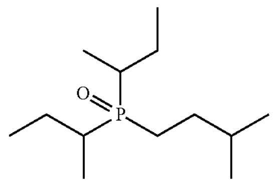 |

General Observations

DIPA compounds are colorless liquids with a density less than water. They are soluble in water or saline at up to 20 mg/mL. When DIPA compounds are applied to the facial skin as an aqueous solution at 1-10 mg/mL or a 1% hydrogel there is little irritation. For certain analogs, contacting the periorbital or malar skin with a solution at a concentration of 1-10 mg/mL produce a sensation of "dynamic cool" that is felt within one minute after application. A single application can evoke this "energizing" sensation, which can counteract fatigue for several hours. DIPA-1-7, especially, has intense dynamic cooling. The mechanisms underlying this "energizing" effect are discussed in detail in this application.

Figure 2:
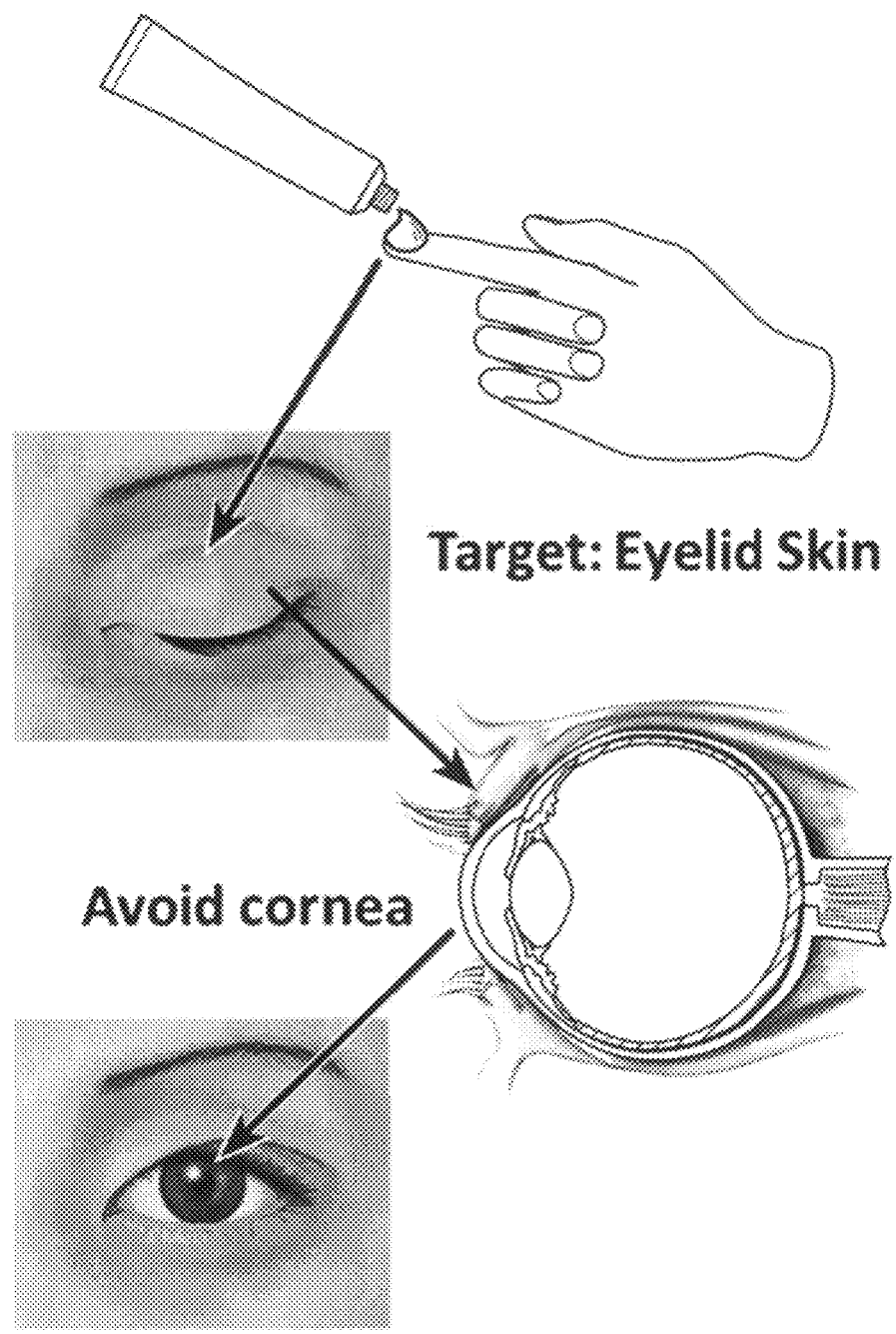
FIG. 2 shows the strategy for "eyeball cooling" in a subject. A DIPA compound of this invention is applied to the eyelid skin with the eyes closed. Contact of the compound to pain fibers of the cornea is avoided. The sensations from the eyelid skin and from the eyeball surface are transmitted via the ophthalmic branch of the trigeminal nerve. When the nerve fibers are activated, the brain perceives the whole orbit as being cooled but without topographical specificity. Thus, the brain is energized by "eyeball cooling", but without pain or stinging from the eye surface.

The method of drug delivery is important to achieve the energizing effect. As shown in FIG. 2, the drug is applied as a 0.5% gel [1.5% carbopol in purified water] to the eyelid skin with the eyes closed, thus avoiding drug contact with the cornea which is densely innervated with pain fibers. The sensory nerves of the eyelids and cornea both send information to the brain via the ophthalmic branch of the trigeminal nerve [$5^{th}$ nerve, V1]. Most likely, the brain does not discriminate topographically between cooling from eyelid skin or from eyeball surface. The net perceived effect is a "dynamic cool eyeball" and brain arousal. Avoidance of drug contact with the corneal surface is a key element of the success of this treatment because the cornea is densely innervated with sensory nerve endings for pain. The penetration of the DIPA compound through the stratum corneum of the eyelid skin is a key factor for delivery and is illustrated in the laboratory data shown in Table 10 and in FIG. 2.

Periorbital administration of DIPA and related DAPA compounds will leave a residue on the eyelid skin. When the eyelids become wet, for example, by taking a shower or sweating, the residual compound will wash onto the cornea and cause stinging and irritation. This will limit the choice of the compound for applications wherein delivery is to the eyelid skin. Among the compounds of Formula 1, DIPA-1-8 and DIPA-1-9 have minimal residual irritation, and so are especially useful for the longer term treatment of ocular discomfort. The efficacy of DIPA-1-9 in the treatment of patients with the "dry eyes syndrome" is demonstrated in Case Study 7. DIPA-1-7 is useful for a shorter term application of cognitivie function.

Both DIPA-1-7 and DIPA-1-8 (and in particular DIPA-1-7) are especially useful for treatment of skin dysesthesias (e.g., skin irritation, itchy skin, or painful skin), heat discomfort, and heat stress. DIPA-1-6 is not as long-acting as DIPA-1-7, but is absorbed more easily across the skin, and is therefore especially useful for systemic applications, e.g., in the treatment of flushing and/or night sweats (vasomotor symptoms).

The effects of DIPA versus the di-sec-butyl congeners were strikingly different in laboratory animals [Table 10]. Perioral or topical application of DIPA [DIPA-1-5, DIPA-1-6, DIPA-1-7] elicits vigorous shaking in the whole animal, but this effect is hardly seen with the di-sec-butyl congeners. This is because DIPA-1-5, DIPA-1-6, and DIPA-1-7 are able to penetrate the membrane barriers in the gut and keratinized skin. The DIPA compounds have pharmacology that is distinct and unusual relative to the other DAPA analogs.

Compositions

One aspect of the present discovery pertains to a composition (e.g., a pharmaceutical composition) comprising a DIPA compound, as described herein, and a pharmaceutically acceptable carrier, diluent, or excipient.

Another aspect of the present discovery pertains to a method of preparing a composition (e.g., a pharmaceutical composition) comprising mixing a DIPA compound, as described herein, and a pharmaceutically acceptable carrier, diluent, or excipient.

In one embodiment, the composition comprises the DIPA compound at a concentration of 0.005-2.0% wt/vol. In one embodiment, the composition is a liquid or semi-liquid composition (lotion, cream, or ointment), and comprises the DIPA compound at a concentration of 0.5-20 mg/mL. In one embodiment, the composition is a liquid composition, and comprises the DIPA compound at a concentration of 1-5 mg/mL. In one embodiment, the composition is a liquid composition, and comprises the DIPA compound at a concentration of 5-10 mg/mL. In one embodiment, the composition is a liquid composition, and comprises the DIPA compound at a concentration of 10-20 mg/mL.

The composition may be provided with suitable packaging and/or in a suitable container. For example, the composition may be provided as a swab, wipe, pad, or towellette (e.g., suitably sealed in a wrap) carrying a DIPA compound or a composition comprising a DIPA compound. Similarly, the composition may be provided as a patch, e.g., a controlled-release patch, e.g., suitable for application to the skin, e.g., the skin above the supraclavicular fossa or the steronomastoid muscle. Similarly, the composition may be provided as an aerosolized spray delivered from a pressurized container. Similarly, the composition may be provided in a manually-activated sprayer (e.g., with a suitable small orifice) linked to a reservoir containing a DIPA compound or a composition comprising a DIPA compound, for example, capable of delivering an unit volume (e.g., of 0.05 to 0.15 mL), for example, to the skin surface.

Use in Methods of Therapy

Another aspect of the present discovery pertains to a DIPA compound, as described herein, for use in a method of treatment of the human or animal body by therapy, for example, for use a method of treatment of a disorder (e.g., a disease) as described herein.

Use in the Manufacture of Medicaments

Another aspect of the present discovery pertains to use of a DIPA compound, as described herein, in the manufacture of a medicament, for example, for use in a method of treatment, for example, for use a method of treatment of a disorder (e.g., a disease) as described herein. In one embodiment, the medicament comprises the DIPA compound.

Methods of Treatment

Another aspect of the present discovery pertains to a method of treatment, for example, a method of treatment of a disorder (e.g., a disease) as described herein, comprising administering to a subject in need of treatment a therapeutically-effective amount of a DIPA compound, as described herein, preferably in the form of a pharmaceutical composition.

Disorders Treated

In one embodiment (e.g., of use in methods of therapy, of use in the manufacture of medicaments, of methods of treatment), the treatment is treatment of: sensory discomfort (e.g., caused by irritation, itch, or pain); a skin dysesthesia; atopic dermatitis; ocular pain and discomfort; heat discomfort; heat stress; flushing and/or night sweats (vasomotor symptoms) in post-menopausal women; post-operative hypothermia; post-anaesthetic shivering; fatigue; tiredness; depression; cognitive dysfunction; and to enhance cognitive function.

Disorders Treated—Sensory Discomfort Etc.

In one embodiment (e.g., of use in methods of therapy, of use in the manufacture of medicaments, of methods of treatment), the treatment is treatment of sensory discomfort.

The term "sensory discomfort", as used herein, relates to irritation, itch, pain, or other dysesthesias (abnormal sensations; such as burning sensations, or feeling the presence of a foreign body, or pins and needles) from the body surfaces. The term implies activation of nociceptors located on sensory nerve endings of the body. Nociceptors are stimulated, for example, by high or low temperatures, mechanical pressure, chemicals (e.g., capsaicin, acidity, pollutants, etc.), injury, inflammation, and inflammatory mediators. A compound, such as DIPA-1-7, that decreases sensory discomfort, can be termed an anti-nociceptive agent.

In one embodiment, the sensory discomfort is irritation, itch, or pain. In one embodiment, the sensory discomfort is caused by a skin dysesthesia. In one embodiment, the skin dysesthesia is skin irritation, itchy skin, or painful skin. In one embodiment, the sensory discomfort is caused by atopic dermatitis. In one embodiment, the sensory discomfort is caused by canine atopic dermatitis. In one embodiment, the treatment is treatment of a skin dysesthesia. In one embodiment, the skin dysesthesia is skin irritation, itchy skin, or painful skin. In one embodiment, the treatment is treatment of atopic dermatitis. In one embodiment, the treatment is treatment of canine atopic dermatitis. In one embodiment, the treatment is treatment of ocular discomfort. In one embodiment, the ocular discomfort is caused by eye strain; eye fatigue; eye surgery; an airborne irritant or pollutant that interacts with the eye surface; extended wear of contact lenses; excessive exposure to the sun; conjunctivitis; or the dry eyes syndrome. In one embodiment, the treatment is treatment of heat discomfort. In one embodiment, the treatment is treatment of heat discomfort for the purpose of improving athletic performance. In one embodiment, the treatment is treatment of heat stress. In one embodiment, the treatment is treatment of flushing and/or night sweats (vasomotor symptoms) in a post-menopausal woman. In one embodiment, the treatment is treatment of post-operative hypothermia or post-anaesthetic shivering. In one embodiment, the treatment is treatment is to convey a sense of refreshment to the skin in a human.

Disorders Treated—Fatigue Etc.

In one embodiment (e.g., of use in methods of therapy, of use in the manufacture of medicaments, of methods of treatment), the treatment is treatment of fatigue, tiredness, or depression. In one embodiment, the treatment is treatment of fatigue. In one embodiment, the fatigue is fatigue caused by chronic illness, ageing, a neurological dysfunction, or a psychological dysfunction. In one embodiment, the fatigue is fatigue caused by cancer or cancer-related treatment. In one embodiment, the fatigue is fatigue caused by anxiety, depression, heat stress, cognitive dysfunction, excessive physical exertion, or excessive mental exertion. In one embodiment, the fatigue is fatigue associated with a decreased ability to think, to concentrate, to study, or to perform work.

Disorders Treated—Cognitive Dysfunction Etc.

In one embodiment (e.g., of use in methods of therapy, of use in the manufacture of medicaments, of methods of treatment), the treatment is treatment of cognitive dysfunction. In one embodiment, the treatment is treatment to enhance cognitive function (e.g., in the healthy as well as the sick). In one embodiment, the enhanced cognitive function is improved hand-eye coordination in a sport. In one embodiment, the enhanced cognitive function is improved performance in a game of chance or of mental skills.

Treatment

The term "treatment," as used herein in the context of treating a disorder, pertains generally to treatment of a human or an animal (e.g., in veterinary applications), in which some desired therapeutic effect is achieved, for example, the inhibition of the progress of the disorder, and includes a reduction in the rate of progress, a halt in the rate of progress, alleviation of symptoms of the disorder, amelioration of the disorder, and cure of the disorder. Treatment as a prophylactic measure (i.e., prophylaxis) is also included. For example, use with patients who have not yet developed the disorder, but who are at risk of developing the disorder, is encompassed by the term "treatment." Treatment to enhance the basal levels of cognitive or physical performance of individuals who are considered normal or healthy is also included.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents.

One aspect of the present discovery pertains to a DIPA compound as described herein, in combination with one or more (e.g., 1, 2, 3, 4, etc.) additional therapeutic agents. The particular combination would be at the discretion of the physician or the pharmacist who would select dosages using his common general knowledge and dosing regimens known to a skilled practitioner.

Examples of additional therapeutic agents include: an anti-inflammatory glucocorticosteroid; an analgesic; a sympathomimetic amine decongestant; an anti-histamine; a local anesthetic; an ophthalmic lubricant; a sunscreen ingredient; an anti-acne agent; a keratolytic agent; an anti-hemorrhoidal agent; an agent for vulvar itch or discomfort; an antibiotic; a skin moisturizer; or an anti-skin ageing agent.

Kits

One aspect of the discovery pertains to a kit comprising (a) a DIPA compound as described herein, or a composition comprising a DIPA compound as described herein, e.g., preferably provided in a suitable container and/or with suitable packaging; and (b) instructions for use, e.g., written instructions on how to administer the compound or composition. The written instructions may also include a list of indications for which the active ingredient is a suitable treatment. The written instructions (e.g., pamphlet or package label) may include the dosage and administration instructions, details of the formulation's composition, the clinical pharmacology, drug resistance, pharmacokinetics, absorption, bioavailability, and contraindications.

Methods of Diagnosis

The DIPA compounds described herein may also be used in diagnosis, for example, diagnosis of allodynia, for example, cold allodynia. More specifically, the DIPA compounds may be used as diagnostic agents for the diagnosis (e.g., differential diagnosis) of cold allodynia.

Allodynia is pain due to a stimulus which does not normally provoke pain. For example, temperature and physical stimuli can provoke allodynia, and it often occurs after injury to a site.

A simple diagnostic tool for differentiating neuropathic pain (e.g., allodynia) from somatic pain is not yet known. A DIPA compound, such as DIPA-1-7, applied to the skin, can be used to provide differential diagnosis of, e.g., cold allodynia.

Routes of Administration

The DIPA compound or pharmaceutical composition comprising the DIPA compound may suitably be administered to a subject topically, for example, as described herein. The term "topical application", as used herein, refers to delivery onto surfaces of the body in contact with air, which includes the skin, the anogenital surfaces, the transitional epithelial surfaces of the orbit, the lips, the nose, and the anus, and the aerodigestive tract (nasal membranes, oral cavity, pharyngeal and esophageal surfaces), lower respiratory tracts, and the lumen of the gastrointestinal tract. Particularly preferred sites of application are the surfaces innervated by the trigeminal and glossopharyngeal nerves which include the scalp, facial skin, periorbital skin, lips, nasal and oral cavities, and the throat. Additional preferred sites are the surfaces of the neck, elbows and knees, which are frequently associated with the pruritus of atopic eczema and psoriasis. Yet another preferred site is the scalp, which can be a site of inflammation in psoriasis and seborrheic dermatitis.

In one embodiment (e.g., of use in methods of therapy, of use in the manufacture of medicaments, of methods of treatment), the treatment is treatment by topical administration. In one embodiment, the treatment is treatment by topical administration to skin. In one embodiment, the treatment is treatment by topical administration to facial skin. In one embodiment, the treatment is treatment by topical administration to periorbital skin, eyelid skin, malar skin, forehead skin, or scalp. In one embodiment, the treatment is treatment by topical administration to skin surface of the orbit, frontal bone, or zygomatic. In one embodiment, the treatment is treatment by topical administration to skin surface of the anus and/or the male or female genitalia. In one embodiment, the treatment is treatment by topical administration to skin above the supraclavicular fossa or the steronomastoid muscle.

The Subject/Patient

The subject/patient may be a mammal, for example, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human. In one preferred embodiment, the subject/patient is a human.

Formulations

While it is possible for a DIPA compound to be administered alone, it is preferable to present it as a pharmaceutical formulation (e.g., composition, preparation, medicament) comprising at least one DIPA compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents.

Thus, the present discovery further provides pharmaceutical compositions, as described above, and methods of making pharmaceutical compositions, as described above. If formulated as discrete units (e.g., swab, wipe, pads, towellettes, gels, lotion, cream, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences,* 18th edition, Mack Publishing Company, Easton, Pa., 1990; and *Handbook of Pharmaceutical Excipients,* 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, lozenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Additionally, the DIPA compound may be used as an adjunct in a pharmaceutical formulation or cosmetic formulation.

Dosage

It will be appreciated by one of skill in the art that appropriate dosages of the DIPA compounds, and compositions comprising the DIPA compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular DIPA compound, the route of administration, the time of administration, the duration of the treatment, other drugs, compounds, and/or materials used in combination, the severity of the disorder, and the species, sex, age, weight, condition, general health, and prior medical history of the patient. The amount of DIPA compound and route of administration will ultimately be at the discretion of the physician, pharmacist, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

Targets for Delivery

Epithelial cells line ducts, cavities and surfaces of organs throughout the body. When there are two or more layers of epithelia, it is called stratified epithelium. Historically, stratified epithelia were divided into two broad categories: keratinized stratified epithelia, and non-keratinized stratified epithelia. Keratinized epithelium, such as the epidermis of the skin, has an exterior layer of dead cells [stratum corneum] composed of keratin proteins that are tough and water-impermeable. By contrast, non-keratinizing stratified epithelia are located on "soft tissues" of the body such as the lining of the nasal and throat cavities and the oesophageal surface. Keratinizing tissues withstand injury better than non-keratinizing tissues. Non-keratinizing epithelial surfaces must be kept moist by glandular (serous and mucous) secretions in order to avoid desiccation.

A layer of keratin is a formidable barrier for drug access to neuronal receptive fields embedded in tissues underneath the keratin.

There are currently no topical antinociceptive (pain-suppressant) compounds that have strong efficacy on sensory discomfort from non-keratinizng stratified epithelium (NKSE). This is especially true for sensory discomfort from the oral cavity, pharyngeal, and oesophageal surfaces.

By experiment, it was discovered that the optimal targets for topical delivery of an agent to counteract fatigue and achieve maximal sensory effects are located on the receptive fields of ophthalmic and maxillary branches of the trigeminal nerve. The preferred sites on the face are periorbital zygomatic=infraorbital, labelled (f), (c), and (a), respectively, in FIG. 1. The periorbital site labelled (f) includes the skin of the eyelids.

FIG. 1 is an illustration of a human head, showing facial sites for testing: (a) infraorbital, (b) buccal cheek, (c) zygomatic, (d) parotid-masseteric Cheek, (e) frontal, and (f) periorbital. Taken from Pilsl et al. [Anatomy of the cheek: implications for soft tissue augmentation. Dermatologic surgery: official publication for American Society for Dermatologic Surgery 38, 1254-62, 2012].

To counteract fatigue or heat stress, the active ingredient is preferably delivered to (a), (c), or (f). Alternatively, if the cooling agent is to be used for flushing and/or night sweats (vasomotor symptoms) in post-menopausal women, it may also be applied to the skin above the supraclavicular fossa or the chest. To reduce sensory discomfort on the skin, the cooling agent may be directly applied to the sites of injury and/or inflammation.

Secondary sites are the skin over the frontal bone and the scalp (labelled (e)), but higher concentrations of cooling agent are required for (e). The other skin sites, namely, buccal cheek, parotid-masseter cheek, periauricular, and chin, lack sensitivity, and sites such as the philtrum, nasal, temporal region, and neck are topographically inconvenient for cooling agent delivery. In practice, the cooling agent can be sprayed or applied (e.g., with a swab or pad or within a gel, lotion, cream or ointment) over the skin of the orbit, the cheekbone (zygomatic), or on the skin beneath the eye, between the cheekbone and nose. The important receptive fields are from the sub-divisions of the trigeminal nerve, namely, the zygomaticfacial nerve of the maxillary nerve (V2) and the supraorbital and supratrochlear brances of the frontal nerve (V1).

One unusual feature of DIPA-1-7 and DIPA-1-8 is that they leave a reservoir in the skin after application, so that after the initial sensations have dissipated, the dynamic cooling sensation returns when the skin is moist again. This feature is especially beneficial for use of DIPA-1-7 and DIPA-1-8 in conditions of elevated environmental temperature. When sweating is activated by heat, the sweat re-solubilizes DIPA-1-7 and DIPA-1-8 and enhances and perpetuates the sensory effect. This self-regulating feedback mechanism makes the effect of DIPA-1-7 and DIPA-1-8 more robust, efficacious, and prolonged.

Methods of Delivery

The delivery of the DIPA compounds can be achieved with the compound dissolved in a solid or semi-solid vehicle, e.g., a cream or an ointment, or in a liquid vehicle, e.g., in a solution, a hydrogel, a lotion, on a swab, wet wipe, or as an aerosolized mist.

An example is the use of a gel as shown in FIG. 2 for delivery onto the eyelid skin.

Gels are semisolid, jelly-like formulations with varying degrees of viscosity. A gel forms a solid three-dimensional network that spans the volume of a liquid medium. Gels are made with gelling agents that cross-link or associate with a liquid phase. Examples of gelling agents are: cellulose derivatives [methylcellulose, carboxymethylcellulose, hydroxylpropylcellulose; carbomers [Carbopol®910, Carbopol®941]; poloxamers [Pluronic®, Tween]; carbomer polymers, and natural polymers such as tragacanth, acacia, gelatin, sodium alginate, alginic acid, and xanthan gum. A single-phase system is a gelling agent plus an active ingredient that dissolves [in water] without visible particles and looks clear. A topical gel optimally liquefies when in contact with skin or mucous membranes. The compounds of Formula 1 are attractive for delivery as gels because they dissolve in water and form a one-phase system at therapeutic concentrations. The methods for formulating topical gels are well-known to the art and extensively described in such sites in Lubrizol.com [a company that manufactures ingredients for cosmetics, personal care, skin care, and eye care].

For a solid or semi-solid vehicle, a preferred concentration of the DIPA compound is 0.01 to 2.0% wt/vol. Unless otherwise stated, wt/vol is measured in units of $g/cm^3$, and so 0.01% wt/vol is obtained from 0.1 mg (0.0001 g) DIPA compound in 1 $cm^3$ of composition; and 2% wt/vol is obtained from 20 mg (0.02 g) DIPA compound in 1 $cm^3$ of composition.

For a liquid vehicle, a preferred delivered volume is 0.05 to 0.15 mL. Such a volume, delivered for example as a spray, does not cause much residual liquid at the delivery site, as the liquid is absorbed.

For a liquid vehicle, a preferred concentration of the DIPA compound is in the range of 0.5 to 20 mg/mL. For the orbit, a preferred concentration is 1 to 5 mg/mL. For the zygomatic and infraorbital skin, a preferred concentration is 5 to 10 mg/mL. For the forehead skin and scalp, a preferred concentration is 10 to 20 mg/mL.

A preferred amount of the DIPA compound delivered at the site of application is 0.01 to 5 mg; for example, 0.1 to 5 mg.

Wiping of the DIPA compound on the target skin can be done with pre-medicated wipes, which are well-known in personal care products, for example, to wipe a baby's skin after a diaper change, or to remove make-up on the face (e.g., Pond's 6"×8" (15 cm×20 cm) Clean Sweep Cleansing and Make-up Remover Towelettes). Usually, these wipes are packaged as a single-use sealed unit or in a multi-unit dispenser. For single units, suitable wrapper materials are those which are relatively vapor impermeable, to prevent drying out of the wipe, and able to form a "peelable" seal. Examples of suitable wipe materials for practicing this discovery include polyamide (20% Nylon)-polyester, rayon (70%)-polyester (30%) formed fabric, polypropylene nonwoven, polyethylene terephthalate (PET), polyester polypropylene blends, cotton, or microfibers (synthetic fibers that measure less than one denier or one decitex).

Alternatively, a solution containing a DIPA compound may be supplied in a reservoir bottle with individual applicators, or as a pre-packaged individual unit. For example, Puritan 803-PCL applicators are ideal cotton-tipped applicators attached to a 3-inch (~7.5 cm) polystyrene rod for delivery of a DIPA compound onto the periorbital skin. Examples of how such applicators can be individually packaged are the SwabDose™ from Unicep Corporation (1702 Industrial Drive, Sandpoint, Id., USA), and the Pro-Swabs from American Empire Manufacuring (3828 Hawthorne Court, Waukegan, Ill., USA). Each applicator tip is saturated by dipping the absorbent material of the tip (e.g., 40 to 100 mg of cotton) in 0.5 to 1.5 mL of an aqueous solution of a DIPA compound and packaged in an individual container.

For application to the face, the individual is instructed to gently apply the cream, lotion, gel, or wet wipe onto, or to spray, to the target facial skin with the eyelids shut, or other skin surface(s). The instructions for application may include teaching the individual to repeat application, or "topping up", to ensure that sufficient composition is delivered to the target. Once the subject has learned what to expect, the individual can adjust the dosage (e.g., by dabbing at the medial or lateral edges of the orbit), as needed, to achieve the desired effect. It has been observed that individuals learn how to effectively apply the cooling agent after one or two trials and do so without risks of discomfort (e.g., eye discomfort).

For application to the anogenital skin or other highly sensitive surfaces, the DIPA compound may be sprayed with a hand-activated manual pump, for example, to deliver volumes of approximately 0.15 mL per activation.

Mechanisms of Action

DIPA-1-7 and DIPA-1-8 produce an anti-fatigue effect and provide relief of heat stress and skin discomfort by evoking a sense of "dynamic cool" at sites of application. The sensation is not a steady cool, cold, or icy-cold sensation, but one of robust freshness, as if suddenly a fresh, cool breeze was blown on the skin (e.g., on the face). This effect, especially with DIPA-1-7 is intense. The neurophysiological basis for this sensation, possible receptor mechanisms, and the significance of dynamic cooling for anti-fatigue, anti-heat stress, and anti-pruritic actions are further discussed herein.

Neurophysiology:

Small myelinated (Aδ) and unmyelinated fibers (C fibers) increase afferent firing rate when skin temperature is lowered, for example, between 35° C. and 15° C. These neuronal signals that detect heat abstraction are transmitted to the central nervous system and generate conscious perception of coolness and cold. When skin temperature is raised from 35° C. and 40° C., firing rates are increased in C fibers and these fibers signal warmth [Hutchinson et al. Quantitative analysis of orofacial thermoreceptive neurons in the superficial medullary dorsal horn of the rat. J. Neurophysiol. 77, 3252-66, 1997]. The receptive mechanisms and "cable lines" for cool/cold and warm are separate and distinct, but reciprocally inhibit each other in the brain and perhaps also in the periphery. The sensory receptors are modality specific and do not respond to mechanical stimulation. At the molecular level, the target binding sites for cooling agents are thought to be located on ion channel receptors that depolarize in response to a drop in temperature. Heat abstraction decreases the threshold for discharge of the receptor, and the facilitated depolarization initiates the axonal responses that create the neuronal signal.

The central response of these neurons has been recorded and studied from rat superficial medullar dorsal horn that responds to innocuous thermal stimulation of the rat's face and tongue [Hutchinson et al., 1997]. Step changes of $-\Delta 5°$ C. stimulated cells with both static firing rates and cells that had mainly dynamic properties [Davies et al. Sensory processing in a thermal afferent pathway. J. Neurophysiol. 53: 429-434, 1985]. Similar studies in cats and humans showed that step decreases in temperatures (dynamic changes), as low as $\Delta 0.5°$ C./second, were readily detectable by neurons and by psychophysical measurements [Davies et al. Facial sensitivity to rates of temperature change: neurophysiological and psychophysical evidence from cats and humans. J. Physiol. 344: 161-175, 1983].

From a study of the spike patterns of neuronal discharge (impulses/second), it was clear that dynamic, and not static firing responses to a change in temperature were the most powerful stimuli for generating coolness/cold sensations That is, the brain "sees"$-\Delta$ ° C./t and not absolute ° C. Thus, a cooling agent that simulates $-\Delta$° C./t on nerve discharge will produce "dynamic cooling".

Relationship of Dynamic Cooling to Anti-Fatigue:

Dynamic cooling (versus static cooling/cold) is essential for an anti-fatigue effect. For example, if one is tired and driving a vehicle, turning on the air-conditioning and blasting the air onto the face will counteract fatigue [dynamic cooling]. But just turning on the air conditioner to lower ambient temperature and being chilled inside the vehicle [static cooling] will not make much of a difference.

The topical therapy for enhanced performance and counteract fatigue described herein circumvents the necessity for systemic drugs that act invasively on brain chemistry. The benefits of the topical therapy are illustrated by the Case Studies described herein.

Receptor Mechanisms:

There is a general view that "TRP-" ion channel receptors (A1, M8, and V1 to 4) are the principal physiological elements for physiological temperature detection. The TRPM8 receptor is the one that responds to sensory/cooling agents such as menthol and icilin [McKemy et al. Identification of a cold receptor reveals a general role for TRP channels in thermosensation, Nature, 416, 52-58, 2002]. TRPM8 is a protein with 1104-amino acid residues and has six transmembrane domains. Activation of this receptor by lowering ambient temperature results in opening of pores of transmembrane loop and non-specific cation entry into the cell. Depolarization of TRPM8 receptors on sensory neurons may then transmit signals primarily via Aδ (and some C) fibres.

While this concept for the role of TRPM8 in sensory physiology may be valid for physical changes in temperature, the interpretation of the sensory effects of chemical agents such as menthol and icilin are more complex. Menthol not only stimulates TRPM8 in vitro, but also TRPV3, a receptor associated with warmth and glycinergic transmission [Macpherson et al. More than cool: promiscuous relationships of menthol and other sensory compounds. Mol Cell Neurosci 32:335-343, 2006: Sherkheli et al., Supercooling agent icilin blocks a warmth-sensing ion channel TRPV3, Scientific World Journal, 2012: 982725, 0.2012: Cho et al. TRPA1-like channels enhance glycinergic transmission in medullary dorsal horn neurons. J Neurochem 122:691-701, 2012]. Thus, menthol and icilin are "promiscuous" cooling agents and their specific sensory effects may not be associated with any one particular receptor protein. A laboratory reagent specific and selective for TRPM8 will be valuable for experiment and is not currently available.

The Applicant has screened a large database of cooling agents but, surprisingly, only DIPA-1-6 and DIPA-1-7 produced super-robust dynamic cooling on skin. DIPA-1-8 also produces strong cooling and its actions are prolonged, but it does not quite have the super "wow" cooling effects of DIPA-1-6 and DIPA-1-7. Other cooling agents are less stimulating or have shorter durations of action and thus less suitable for the uses contemplated herein. Thus, the DIPA compounds, by contrast to menthol and icilin, are ideal selective reagents to investigate TRPM8 function.

It may be concluded that DIPA-1-7 and DIPA-1-8 bind to a site on a voltage-gated ion channel receptor located on a nerve ending that is sensitive to a decrement in physical temperature. This event facilitates neuronal depolarization to a cooling/cold signal, and an action potential is transmitted via Aδ and C fibers towards the central nervous system. If the nerve ending is located on the facial skin, the signal is recordable from dorsal surface of the trigeminal nucleus in the brainstem. Further rostral transmission and integration of signals give rise to the perception of coolness/cold and its topographical association with the site of stimulation.

When one examines the structure-activity relationships (SAR) of the DIPA compounds, it is noted that when $R_1=R_2$=isopropyl and $R_3$=n-hexyl ($C_6$) or n-heptyl ($C_7$), then dynamic cooling is observed. Strong cooling of long duration is also obtained with $R_3$=n-octyl ($C_8$). However, when $R_1=R_2$=sec-butyl and $R_3$=n-butyl to n-octyl ($C_4$ to $C_8$), dynamic cooling is partially observed, but with much less intensity. As shown in the studies described herein, this distinction between di-sec-butyl and di-iso-propyl compounds is also seen in animal studies on shaking behaviour, an indicator of cooling actions in the rat (because shaking is inhibited by heat).

Shaking behaviour is a rapid alternating contraction of the supination and pronation muscles about the spinal axis, and can be readily observed and counted. Fur-coated and feathered animals—when wet and cold—shake, like a wet dog [Dickerson et al., Wet mammals shake at tuned frequencies to dry. J. Royal Society, Interface 9, 3208-3218, 2012; Ortega-Jimenez, V. M. et al. Aerial shaking performance of wet Anna's hummingbirds. J. Royal Society, Interface 9, 1093-9, 2012; Wei, Pharmacological aspects of shaking behavior produced by TRH, AG-3-5, and morphine withdrawal, *Federation Proc.* 40: 1491-1496, 1981].

"Wet-dog shaking" has been studied in detail in animals. Rats can shake their head, the upper torso, or the shaking can be sufficiently violent to affect the whole body and make the animal lose its balance. DIPA-1-7 and DIPA-1-8 elicit the vigorous type of shaking. The purpose or survival value of shaking to fur-coated and feathered organisms is to remove water droplets trapped on or near the skin. Removal of the water droplets on or near the skin by shaking reduces the organism's need to expend energy to remove the water by evaporation. The likely equivalent behaviour to shaking in humans is shivering, a condition caused by generalized sensations of coolness/cold. Human subjects recovering from the deep hypothermia of anaesthesia manifest vigorous shaking; a condition called post-anaesthetic shivering.

Icilin (1-[2-hydroxy]-4-[3-nitrophenyl]-1,2,3,6-tetrahydropyrimidine-2-one) induces vigorous shaking in rats [Wei. Chemical stimulants of shaking behavior. J. Pharmacy and Pharmacology 28: 722-724, 1976], Surprisingly, two potent p-menthane carboxamide cooling agents [(R)-2-[((1R,2S,5R)-2-isopropyl-5-methyl-cyclohexanecarbonyl)-amino]-propionic acid ethyl ester, and [((1R,2S,5R)-2-isopropyl-5-methyl-cyclohexanecarbonyl)-aminoFacetic acid isopropyl ester], which have $EC_{50}$ values similar to icilin at the TRPM8 receptor, do not evoke shaking (when injected at 50 mg/kg s.c. in male rats and observed for 1 hour. Icilin activation at the TRPM8 receptor is abrogated by a G805A mutation at the second to third transmembrane loop, but the effects of menthol are not affected. It is likely that DIPA-1-6, DIPA-1-7, and DIPA-1-8 also have specific sites of binding and activation on the TRPM8 receptor which are not shared by menthol or p-menthane carboxamides. Recent studies by Wei and Kuhn have shown that DIPA-1-6 and DIPA-1-7 are still active on TRPM8 receptors with the G805A mutation.

The studies described in Watson et al., 1978 [New compounds with the menthol cooling effect. J. Soc. Cosmet. Chem. 29: 185-200, 1978] show that the presence of a polar oxygen moiety capable of acting as an acceptor of a hydrogen bond from the receptor is essential for bioactivity. A Hückel molecular orbital calculation (using Molecular Modelling Pro v6.0.3, ChemSW Inc, Fairfield, Calif. 94534, USA) on the isopropyl analogs versus the sec-butyl analogues favours a slightly higher partial negative charge (0.007 e) on the oxygen in the sec-butyl entities, suggesting that the sec-butyl substituents facilitate a higher affinity of the oxygen to the hydrogen binding site of the receptor. Thus it is possible that isopropyl, with a "looser" affinity can associate and disassociate with the receptor more rapidly, favouring the generation of a dynamic onset and offset response of the receptor. This rapid interaction with the binding site will favour a more "dynamic" and intense stimulation of cooling and give rise to the phenomenon known as shaking.

Another possibility is that DIPA-1-7 has a dual action on TRPreceptors, so that it stimulates TRPM8 and, at higher concentrations, stimulates TRPV1. The dual action will give a cold-hot synergy that might lead to a more dynamic cooling sensation.

TRPM8, TRPA1, and TRPV1 Receptor Assays:

The in vitro effects of test compounds were evaluated on cloned hTRPM8 channel (encoded by the human TRPM8 gene, expressed in CHO cells) using a Fluo-8 calcium kit and a Fluorescence Imaging Plate Reader (FLIP-RTETRA™) instrument. To examine the specificity of the test compounds, further tests were conducted on TRPV1 channels (human TRPV1 gene expressed in HEK293 cells) and TRPA1 channels (human TRPA1 gene expressed in CHO cells). The assays were conducted by ChanTest Corporation, 14656 Neo Parkway, Cleveland, Ohio 44128, USA.

Selection of Active Ingredient

Ideally, an active pharmaceutical ingredient (API) formulated for delivery to the keratinized skin should be stable, non-toxic, and sufficiently long-acting and potent to activate the mechanisms that result in an anti-fatigue, anti-heat, or anti-nociceptive effect. The API should be dissolved and evenly dispersed in a composition so that during manufacture the formulation maintains a constant concentration. The final product should meet standards of cleanliness and sterility. For purposes of formulation, the API can be a liquid at standard conditions of temperature and pressure (STP) and that is evenly dissolved in aqueous solutions at neutral pH and/or isotonicity. Sterility of the final product can be optimally achieved by using purified reagents and filtration through micropore filters, heating, or irradiation. Standard excipients, such as emulsifying agents, isotonic saline, solvents, stabilizing agents, and preservatives, may be added to optimize the formulations, but the important ingredients should be preferably soluble in aqueous media such as purified water or a standard dermatological solvent.

For a given individual, the perceived sensation is a function of the particular cooling agent, the dose, the vehicle used to carry the cooling agent, the method of topical delivery, and the nature of the target surfaces. The Applicant has screened a number of candidate compounds, such as p-menthane carboxamides, on the facial skin (Wei. Sensory/cooling agents for skin discomfort. Journal Skin Barrier Research 14: 5-12, 2012). The studies here identify DIPA-1-6, DIPA-1-7, and DIPA-1-8 as having the preferred desired properties of an ideal anti-fatigue, anti-heat, and anti-nociceptive agent.

To summarize, the design concepts that lead to the selection of DIPA-1-6, DIPA-1-7, and DIPA-1-8, as being suitable agents are:

The definition of a rationale for using a "dynamic cool" sensation around the orbit and zygomatic to combat fatigue, and describing the neurophysiology and mechanisms of this action. This sensory effect in unusual and found in the DIPA compounds but not found with structurally similar compounds.

Devising a delivery method for the API which avoids contacting nociceptors on the cornea because that will result in sting/pain and be aversive and not practical.

Finding an ideal compound (API) by experiment: DIPA-1-7 is water soluble (a clear solution is obtained at up to 20 mg/mL in distilled water), stable to heat, and exerts a "dynamic cool" sensation for five to seven hours at an applied concentration of 1 to 10 mg/mL. Tachyphylaxis does not develop to repeat applications.

Defining the receptor targets of these compounds in vitro, and the selectivity of the chosen API.

Defining an in vitro isolated nerve preparation that shows an anti-nociceptive action of DIPA-1-7, and showing that this effect is abrogated on the nerve from a TRPM8 knockout mouse.

Defining an animal model (of "wet-dog shakes") that will illustrate the "dynamic cool" properties and allow further study of mechanisms of action and the selective differentiation of various analogs.

Conducting tests in human volunteers that show efficacy of the DIPA compounds for reducing fatigue caused by chronic illness and heat stress, and for increasing mental energy levels in the normal person.

Conducting tests in human volunteers that show DIPA compounds, especially DIPA-1-7, is effective for relieving sensory discomfort of the skin, and thus may be used as an anti-nociceptive or anti-pruritic agent, or as a diagnostic tool for evaluating skin dysesthesias.

Applications

The DIPA compounds, when applied to keratinized skin, have sensory/cooling effects that mimic heat abstraction, but without a change in tissue temperatures. These compounds, especially DIPA-1-5, DIPA-1-6, DIPA-1-7, and DIPA-1-8, can also penetrate the skin barrier, reach nerve endings in the epidermis and dermis, and enter the systemic circulation to exert cooling actions. These effects are obtained at small volumes, e.g., 0.1 to 0.5 mL, applied at a concentration of 1 to 20 mg/mL, or 0.1 to 2% wt/vol. The onset of effect is rapid, less than 5 minutes, and the sense of coolness is robust, refreshing, and strong. Compounds with similar bioactivity on the keratinized skin are not currently known or used in cosmetic or therapeutic applications. A number of new applications are possible with a molecule having such unusual properties.

For conditions of increased sensations of perceived heat stress, DIPA-1-7 can also be used, for example, to increase athletic performance, to counteract the discomfort of vasomotor symptoms, and to counteract the discomfort of inflammation. In normothermic conditions, DIPA-1-7 applied to the facial skin may be used to enhance cognition and to alert and increase vigilance. DIPA-1-7 may also be used as a diagnostic agent for cold allodynia and hyperalgesia, as a laboratory reagent to characterize TRPM8 functions, and as an adjunct in the formulations of numerous topical pharmaceuticals.

Heat Stress:

Thermal comfort is a technical term used by air-conditioning engineers to define "a state of mind in humans that expresses satisfaction with the surrounding environment." Maintaining thermal comfort for occupants of buildings or other enclosures is one of the important goals of architects and design engineers. For most people, the room temperature for thermal comfort is 25° C. (77° F.). Careful studies have documented that work performance and productivity (output/input) drop by 2% for every increment of +1° C. above 25° C. up to 33° C. At office temperatures of 28-30° C. (82-86° F.), there is increased sweating and complaints of headache, drowsiness and dullness, difficulty in concentrating, and physical discomfort. For example, studies have shown that increasing the indoor air temperature of a call center from 25° C. to 26° C. decreased the call response rate from 7.79 to 7.64 calls/hr, a 1.9% loss [Tanabe et al., 2007]. An ambient temperature above 25° C. is thus a form of heat stress.

Energy consumption of buildings in China account for at least one-quarter of the country's energy use, and sales of air-conditioning systems in Brazil and India are on an exponential increase. This rise in energy use has raised further concerns about global warming, but as most populations now work indoors, energy costs must be balanced against worker productivity. Basically, a worker's efficiency is better when he or she is kept cool. A method for combating mental lassitude from a hot environment, without incurring expenditures for energy, would have economic benefits. In the Case Studies describe herein, it was found that application of DIPA-1-7 to the facial skin of a student preparing for exams was useful in overcoming the discomforts of heat. The application of a DIPA-1-7 0.5% gel onto the facial skin, especially on the skin of the eyelids, and also on the skin of the neck, also provides relief from heat.

Athletic Performance:

It is a natural desire of humans to want to perform better, either physically or mentally. Recently, there has been an enthusiastic surge of interest in the use of cryotherapy to improve athletic performance. Cryotherapy is defined as "... the lowering of tissue temperature (locally or generally) by the withdrawal of heat from the body to achieve a therapeutic objective ..." External pre-cooling by heat abstraction, for example, by immersion in ice or by wearing a vest packed with ice, can improve work endurance in a hot environment (see, e.g., Marino et al., 2002). An increase in physical work output of ~5% can be shown for tasks of approximately 30 min [Grahn D A et al. Heat extraction through the palm of one hand improves aerobic exercise endurance in a hot environment. J Appl Physiol 99:972-978, 2005] Heat exhaustion limits work and this occurs when core body temperature approaches 40° C. (104° F.). Pre-cooling (or internal cooling, for example, by drinking an ice slurry) slows down the rate of heat accumulation.

Surprisingly, the improvement in athletic performance can be attained by increasing the perception of coolness, without modifying core temperature. Investigators showed that trained marathon runners wearing a commercial cooling collar (Black Ice LLC, Lakeland Tenn.) extended the time to reach volitional exhaustion by 13.5% [Tyler et al. Cooling the neck region during exercise in heat. *J. Athletic Training*, 46, 61-68, 2011]. Cooling of the neck dampened the perceived level of thermal strain and delayed the point of voluntary termination of exercise. Participants tolerated a higher body temperature and heart rate when their neck regions were cooled.

In several studies with menthol, a chemical that produces sensations of coolness without a change in skin or core temperatures, it was noticed that an increased perception of cooling, without a change in core body temperature, may also enhance better physical performance. This effect was unexpected and attributed to menthol being a "positive" placebo [Gillis D J et al. The influence of menthol on thermoregulation and perception during exercise in warm, humid conditions. Eur J Appl Physiol 2010; 110:609-618; Schlader et al. The independent roles of temperature and thermal perception in the control of human thermoregulatory behavior. Physiol Behav 103:217-224, 2011]. The surface of the face is densely innervated with nerve endings that detect temperature. The peripheral cool/cold detection system is associated with specific nerve fiber discharges and precisely regulated so ±1° C. is easily discriminated. Over 92% of thermoceptive units on the face, especially around the lips, respond to cooling and these neurons are tonically active at room temperature (see, e.g., Hutchison et al., 1997).

It is likely than an agent such as DIPA-1-7 or DIPA-1-8, applied to the face, neck region, or chest will decrease heat discomfort and improve athletic performance. Vasomotor Symptoms ("Hot Flushes/Night Sweats" in Post-Menopausal Women):

Flushing (vasodilation) and sweating occur on the body when the brain's thermoregulatory system perceives a need to lower body temperature. After menopause, at least one-third of women experience "hot flushes" (i.e., brief but repetitive episodes of feeling warm and flushed, and daytime and nighttime sweating). Replacement estrogens may alleviate symptoms but there are uncertainties if hormone replacement therapy (HRT) is safe. Sweating episodes that occur at night and in the early morning hours are especially inconvenient because the bed-sheets become wet and it is burdensome to change the bed-sheets on a daily or frequent basis. Episodes of "hot flushes/night sweats" can occur as often as on average 14 episodes per week. Aside from HRT, current alternative methods of therapy, such as yoga, acupuncture, and phytoestrogens, have limited if any effectiveness.

The DIPA compounds are potent agents that can cross the skin barrier and be absorbed into the bloodstream and exert systemic effects. One possible method of treating vasomotor symptoms may be to topically administer DIPA-1-6 or DIPA-1-7 via a controlled-release patch. The systemic effects of the DIPA compound will then give rise to cooling sensations to counteract activation of central heat-loss mechanisms (vasodilatation and sweating). The patch may be applied at night to a convenient location of the body, e.g., the skin above the supraclavicular fossa or the skin above the sternomastoid muscle, and the released DIPA compound would then inhibit the "night sweats." Alternatively, the DIPA compound (e.g., DIPA-1-5, DIPA-1-6, or DIPA-1-7) can be applied locally to the skin as a gel, lotion, or cream.

Cognitive Enhancement:

Humans want to perform better, either physically or mentally. Chemicals that enhance performance belong to two categories: those that increase physical capabilities, e.g., anabolic steroids or vitamins, and those that increase cognitive functions. Drugs that are "cognitive enhancers" (CEs) are also called nootropic drugs or neuroenhancers, and include substances such as caffeine, amphetamines, methylphenidate, nicotine, donepezil, and modafinil. The CEs are designed to enhance the individual's capacity for tasks such as abstract thinking, attention, attitude, brainstorming, comprehension, recognition, creative thinking, critical thinking, increasing curiosity, executive functions, decision making, eidetic memory, emotions and feelings, goals and goal setting, imagination, intelligence, introspection, lateral thinking, learning, memory, mental calculation, motivation, perception, personality and recollection (recall).

Conscious perception of the visual world depends on the visual system to capture image patterns on the retina and to deliver it to the brain for cognition and understanding. Cognitive functioning is the sum of memory, intelligence, creativity and attention. Human attention is further divided into attentional tone (the state of vigilance) and selective attention (the ability to focus on and to execute a task without being distracted). The brain network for attention and its pharmacology has been the subject of reviews (Lanni et al. Cognition enhancers between treating and doping the mind. Pharmacological Research 57: 196-213, 2008]. The neurotransmitter mechanisms of some CEs have been investigated. Drugs such as amphetamines and methylphenidate increase vigilance via catecholaminergic pathways and nicotine and donepizil may affect selective attention via cholinergic pathways. The visual system is especially important to an organism's survival and it is estimated by neurophysiologists that at least 90% of the organism's brain activity is focused on processing and interpreting visual sensory input.

Not all chemicals that affect brain/behavior enhance performance. For example, alcohol (ethanol) and cannabis are not cognitive enhancers. A decrement in cognitive performance is called cognitive dysfunction (or impairment) and can be manifested as fatigue, sleepiness, loss of memory, and inability to learn, to make decisions, to complete tasks, or to follow instructions. Cognitive dysfunction leads to decreased job productivity, transportation system accidents, inability to perform, and daytime fatigue/sleepiness. Many conditions can lead to cognitive dysfunction and impairment including ageing, anxiety, depression, Alzheimer's disease, strokes, Parkinson's disease, narcolepsy, insomnia, disruption of circadian rhythms, obstructive sleep apnea, and depression.

Drugs such as caffeine, amphetamines, methylphenidate, nicotine, donepezil, and modafinil have been used to enhance cognition and to treat fatigue. These compounds act invasively on brain chemistry. That is, the drugs require access of the active agent to the bloodstream, and from there to central nervous system, to act upon enzymes or receptors. Drugs such as amphetamines and nicotine have addiction liability. Even caffeine can over-stimulate the nervous system and causes palpitations, irritability, tolerance, and dependence. There is a need for alternative methods for cognitive enhancement and the treatment of tiredness.

Use of drugs such as CEs in the healthy, e.g., in the academic and business environment, has been the subject of much recent debate [Talbot, 2009, "Brain gain. The underground world of "neuroenhancing" drugs", *The New Yorker*, 27 Apr. 2009; H. Greely. Towards responsible use of cognitive-enhancing drugs by the healthy. Nature 456: 702-706, December 2008, 2008]. Here the proposed method of CE is achieved by topical administration of an agent with a "dynamic cool" effect onto the external surface of facial skin and there is no direct invasion of brain chemistry.

It may be asked why cognitive functions should be enhanced by a DIPA compound. If you ask a person from a cold climate (e.g., Norway, Russia, or Korea) if frigid air on the face will wake you up and think more clearly, they will state that this in a known experience and an obvious fact. Frigid cold weather makes people think more clearly. The dynamic cool produced by DIPA-1-7 is a similar alerting event.

Without wishing to be bound by any particular theory, the Applicant proposes the following hypothesis as an explanation for this phenomenon. Approximately 200 million years ago certain organisms acquired the ability to control metabolic heat production (endothermy) and to maintain a constant internal body temperature (homeothermy). This evolutionary transition, from a "cold-blooded" to a "warm-blooded" physiology, enabled such species to better adapt and to survive in a variable environment. Although humans primarily evolved in a warm habitat, migration has also exposed the species to cold. Coolness is the first signal to warn of the need for heat conservation and is a pervasive and dominant neuronal signal for ensuring the organism's survival because the metabolic machinery of the organism operates efficiently at, and is dependent on, a constant temperature. In the presence of cold, an organism thinks and plan for survival. This circuitry is built into the brain, and serves as a template for arousal and enhancement of cognitive function.

In summary, the applicant has found that applying a dynamic cooling effect to the facial skin, especially the periorbital area, creates an enhancement effect on cognition.

Illness-Related Fatigue:

Feeling tired, weary, and fatigued is a common experience and is considered an inconvenience that may be resolved by taking a nap, drinking a cup of coffee, or stopping whatever activity that brought it on. In many disorders, however, fatigue is a non-specific symptom with adverse consequences.

Fatigue, and its operational deficits, are recognized in this definition by the Federal Aviation Administration [Salazar, 2013: Fatigue in aviation. Medical Facts for Pilots. Publication OK-07-193, prepared for FAA Civil Aerospace Medical Institute]:

"Fatigue is a condition characterized by increased discomfort with lessened capacity for work, reduced efficiency of accomplishment, loss of power or capacity for work, reduced efficiency of accomplishment, loss of power or capacity to respond to stimulation, and is usually accompanied by a feeling of weariness and tiredness" (see, e.g., Salazar, 2013).

Fatigue is recognized as an important problem for patients with advanced progressive illness, especially cancer, as fatigue negatively affects physical, psychological, social and spiritual well-being, and quality of life (QOL) [Minton et al. Drug therapy for the management of cancer-related fatigue, Cochrane. Database. Syst. Rev, Jul. 7, 2010]. This symptom is identified as a condition that requires management and research priority. For cancer-related fatigue: a consensus definition is "a common, persistent, and subjective sense of tiredness related to cancer or to treatment for cancer that interferes with usual functioning".

Conditions that cause fatigue include: anxiety, boredom, depression, disruption of circadian rhythm or sleep, heavy physical exertion, excessive mental activity, treatment for cancer, chronic illness, and heat stress [see, e.g., Salazar, 2013; Stasi et al. Cancer-related fatigue: evolving concepts in evaluation and treatment. Cancer, 98, 1786-801, 2003]. The definition used by the National Cancer Institute for fatigue is a condition marked by extreme tiredness and inability to function due lack of energy. Fatigue may be acute or chronic (greater than 1 month duration), and, depending upon the accompanying symptoms, severity, and duration, it may be further classified as mild, moderate, or severe. Fatigue is a subjective sensation and its primary symptom is a complaint of tiredness. [National Cancer Institute: PDQ® Fatigue. Bethesda, Md.: National Cancer Institute. Date last modified Nov. 4, 2011. Available at: http://cancer.gov].

Assessment instruments specific for fatigue have been developed such as the Brief Fatigue Inventory, the Cancer Fatigue Scale, the Fatigue Assessment Instrument, and the Multidimensional Fatigue Inventory. The important questions asked of patients are: (1) Do you feel or have you ever felt unusually tired? (2) If yes, can you indicate how tired you feel on average on a scale from 0 to 10? (3) How much does this tiredness affect your daily life activities?

Related symptoms of fatigue are: complaints of generalized weakness or limb heaviness, diminished concentration or attention, diminished energy, increased need to rest, decreased interest in engaging in usual activities, insomnia or hypersomnia, experience of sleep as un-refreshing or non-restorative, difficulty in completing daily tasks attributed to feeling tired, perceived problems with short-term memory, and changes in emotional reactivity (e.g., sadness, frustration, or irritability). If five or more these symptoms are present every day or nearly every day during a 2-week period, then a diagnosis of medical fatigue is made. Using these questionnaires it has been estimated that fatigue is present at the time of diagnosis in approximately 50% of cancer patients, and can increase to 60-96% of cancer patients during treatment.

In addition to cancer, other serious illnesses in which fatigue has been examined for interventions include chronic obstructive pulmonary disease, motor neuron disease, cystic fibrosis, dementia, Parkinson's disease, human immunodeficiency virus/acquired immune deficiency syndrome, and multiple sclerosis. Recognised potential causes of fatigue include anemia, dehydration, infection, malnutrition, pain, depression, disturbed sleep, anxiety, hypothyroidism, disease progression, and muscle wasting and deconditioning. A feature of fatigue in these patients includes feeling tired without exertion and even after resting. Patients complain of a reduced capacity to carry out the normal activities of daily living, slow physical recovery from tasks, and diminished concentration.

Management of fatigue includes drugs such as antidepressants, analgesics, stimulants, anxiolytics and nutritional supplements. Non-drug methods include counseling on improved sleep practices, physical exercises, and relaxation techniques. Erythropoietin and darbepoetin, drugs that stimulate red blood cell production, are effective, but may decrease survival, and this adverse effect limits their use. In reviews of the literature, no drugs that work as central nervous stimulants other than methylphenidate exhibit clearly identified benefits to counter fatigue [Talbo, 2009.]. Fatigue is considered a condition that requires research priority because other adverse effects of cancer treatment, namely, pain and nausea, are relatively well-managed, but fatigue is not.

Topical application of a "dynamic cool" agent such as DIPA-1-7 onto facial skin may have utility to counter-act fatigue, refresh, and to invigorate.

Sensory Discomfort from Body Surfaces:

The potent "dynamic cool" sensations produced by DIPA-1-7 and DIPA-1-8 were further evaluated for anti-itch (and other anti-nociceptive) effects on skin. As shown in the Case Studies described herein, a 20 mg/mL solution, applied with a cotton-tipped applicator potently stopped itching and discomfort caused by contact dermatitis in three individuals.

A topical medication that can relieve sensory discomfort has many applications including:
a) alleviation of irritation, itch and pain from various forms of dermatitis (atopic, contact, and irritant);
b) pain from burned, traumatized, diseased, anoxic, or irritated skin (e.g., skin damaged by laser surgery, diabetic ulcers, sunburn, radiation), and from procedures related to wound debridement and wound healing;
c) itch and discomfort from skin infections, insect bites, sunburn, photodynamic treatment of skin (e.g., actinic keratoses, basal cell carcinoma), lichen sclerosus;
d) pruritus due to xerosis [especially dry skin itch of the elderly], psoriasis, or seborrheic dermatitis;
e) stomatitis, cheilitis, itching of the lips from cold sores or gingivitis;
f) pruritus ani, hemorrhoidal discomfort, pain from anal fissures, pain or itch from anal fistulas, pain from hemorrhoidectomy, perineal inflammation, anogenital skin inflammation and discomfort due to various local causes such as incontinence, diaper rashes, perineal inflammation;
g) vulval pruritus and pain (e.g., from candidiasis or idiopathic, such as vulva vestibulitis and vulvodynia), dyspareunia, anogenital infections, including warts and sexually transmitted diseases, fungal infections, viral infections of the skin (especially in immunocompromised patients);
h) nostril and nasal or upper airway discomfort from breathing obstruction, e.g., congestion, rhinitis, asthma, bronchitis, emphysema and chronic obstructive pulmonary diseases, dyspnea, sleep apnea and snoring; and
i) conjunctivitis, ocular surface irritation, pain from trauma and corneal abrasions, and pain from eye surgery.

Of special interest, is the use of DIPA-1-7 and DIPA-1-8 for scalp itch, e.g., in seborrheic dermatitis and psoriasis; these end-points being unmet medical needs. DIPA-1-7 may also be used to refresh the skin before application, or after removal of, cosmetics from the skin, to reduce the irritant effects of benzyoyl peroxide in the treatment of acne, and to reduce sebum secretion and the appearance of an "oily" skin.

Diagnostic Agent for Allodynia:

Allodynia (pain due to a stimulus that does not usually provoke pain) and hyperalgesia (increased pain from a stimulus that usually provokes pain) are prominent symptoms in patients with neuropathic pain [Was Jensen et al., 2014). Allodynia and hyperalgesia in neuropathic pain: clinical manifestations and mechanisms. Lancet Neurology, 13: 924-935, 2014]. Patients with neuropathic pain frequently suffer from painful sensations induced by normally innocuous skin cooling, a condition called cold allodynia [Wasner, G. et al. The effect of menthol on cold allodynia in patients with neuropathic pain. Pain medicine (Malden, Mass.) 9, 354-8, 2008]. Cold allodynia is frequent in diabetic patients with pain, but a simple diagnostic tool for differentiating neuropathic pain from somatic pain is missing. An agent such as DIPA-1-7 applied to the skin may be useful for such diagnosis and aid in the selection of the best method for therapy. A 40% menthol solution in alcohol has been used as a challenge agent, but the results in the clinic have been ambiguous [Binder J. et al. Topical high-concentration (40%) menthol-somatosensory profile of a human surrogate pain model. J. Pain, 12: 764-773, 2011].

Laboratory Reagent for the Study of TRPM8 Function

Menthol and icilin are traditional laboratory tools for the study of TRPM8 in vitro and in vivo. The limitations of these molecules for characterizing TRPM8 functions are well-known: namely, the lack of receptor selectivity, and the difficulty of preparing formulations for administration [Yin et al. Therapeutic opportunities for targeting cold pain pathways. Biochemical Pharmacology, 2014]. Solvents such absolute ethanol and dimethylsufloxide are used to dissolve menthol crystals and icilin, respectively. These solvents independently have pharmacological actions and may distort the effects of the active ingredient. Water-soluble laboratory reagents such as DIPA-1-5, DIPA-1-6, DIPA-1-7, and DIPA-1-8, will greatly facilitate experimental investigations of TRPM8 pharmacology and physiology. These compounds have not been used in the prior art.

Prevention of Post-Operative Hypothermia and Post-Anaesthetic Shivering:

Surgical patients with mild peri-operative hypothermia (33 to 36.4° C.) and post-anaesthetic shivering have a greater risk of adverse outcomes, including events such as decreased wound healing, increased bleeding, and morbid cardiac events [Buggy et al. Thermoregulation, mild peri-operative hypo-thermia and post-anaesthetic shivering. *Brit. J. Anaesth.* 84: 615-628, 2000]. A study has suggested that a TRPM8 agonist such as menthol, by producing cold sensations, can elevate core temperature [Tajno et al Cooling-sensitive TRPM8 is thermostat of skin temperature against cooling, PloS one 6: 2011]. An agent such as DIPA-1-7, by increasing sensitivity to cold, may be an useful as a drug treatment against post-operative hypothermia. In the rat, injection of DIPA-1-7 induces shaking, elevation of body temperatures, and a shortening of the duration of pentobarbital anesthesia, as measured by recovery of the righting reflex. These pharmacological actions will counter the depressive effects of anesthetics on body temperature.

Pharmaceutical Adjunct:

In pharmaceuticals or cosmeceuticals, the term "adjunct" is an additional substance, treatment, or procedure used for increasing the efficacy or safety of the primary substance, treatment, or procedure or for facilitating its performance. The DIPA compounds relieve sensory discomfort of the skin, have anti-nociceptive activity, and are active at less than 1 minute after application. They are ideal adjuncts for pharmaceuticals and for cosmetics applied to the skin.

If the primary substance is an irritant, the adjunct may be used to decrease irritancy, and hence improve patient tolerance and compliance. For example, an adjunct such as DIPA-1-7 can be added an anti-acne preparation containing benzoyl peroxide. Benzoyl peroxide, the primary substance, works as a skin peeling agent, increases cell turnover, and reduces *P. acnes*, but it is an irritant and can cause burning, swelling, and pain when applied to the skin. Similarly, imiquimod (Aldara®), which is used as a primary substance to treat genital warts and skin cancer can cause blistering and pain, and an adjunct such as DIPA-1-7 or DIPA-1-8 may increase patient acceptance and compliance in the use of this drug.

An adjunct such as DIPA-1-7 may be used to increase the "apparent" efficacy of another primary ingredient, and thereby improve patient satisfaction and adherence to a dosage schedule. For example, DIPA-1-7 at about 0.5 to 2%, stops itching within minutes after application. If combined with an anti-inflammatory steroid, the preparation may be more desirable than the anti-inflammatory steroid alone, which takes longer to act. Anti-inflammatory steroids, such as hydrocortisone, triamcinolone, and clobetasol are used for sensory discomfort of the skin in disorders such as insect stings, contact dermatitis, atopic eczema, and psoriaisis. The presence of DIPA-1-7 as an adjunct, in addition to helping to stop the itch, may help reduce the dose or the frequency of application of the primary ingredient, yet achieve an equivalent therapeutic effect. This adjunct benefit will be especially beneficial in the use of skin steroids because of the well-known undesirable effects of collagen degradation, tissue thinning, and increased susceptibility to infections. An adjunct that reduces dosage or promote greater efficacy of the primary ingredient has value. Other primary anti-pruritics are aluminum acetate, and strontium chloride or strontium nitrate.

For skin disorders, compositions of the present discovery may also be used as adjuncts for procedures such as phototherapy, laser therapy, cryotherapy, or UV-therapy of the skin.

Pharmaceuticals that may be used, in combination or in sequence with adjunct DIPA compounds include anti-inflammatory steroidal agents, anti-inflammatory analgesic agents, antihistamines, sympathomimetic amine vasoconstrictors, local anesthetics, antibiotics, anti-acne agents, topical retinoids, drug for genital warts and skin cancer, drugs for wrinkles and ageing skin, anti-hemorrhoidal agents, drugs for vulvar itch, skin moisturizers, and agents for keratolysis.

Examples of steroidal anti-inflammatory agents include hydrocortisone, clobetasol, clobetasol propionate, halobetasol, prednisolone, dexamethasone, triamcinolone acetonide, fluocinolone acetonide, fluocinonide, hydrocortisone acetate, prednisolone acetate, methylprednisolone, dexamethasone acetate, betamethasone, betamethasone valerate, flumetasone, fluticasone, fluorometholone, beclomethasone dipropionate, etc.

Examples of anti-inflammatory analgesic agents include methyl salicylate, monoglycol salicylate, aspirin, indomethacin, diclofenac, ibuprofen, ketoprofen, naproxen, pranoprofen, fenoprofen, sulindac, fenclofenac, clidanac, flurbiprofen, fentiazac, bufexamac, piroxicam, pentazocine, etc.

Examples of antihistamines include diphenhydramine hydrochloride, diphenhydramine salicylate, diphenhydramine, chlorpheniramine maleate, promethazine hydrochloride, etc.

Examples of sympathomimetic amine vasoconstrictors include phenylephrine hydrochloride, oxymetazoline, naphazoline, and other imidazoline receptor agonists used for nasal decongestant activity and for redness and vasodilatation on the ocular surfaces.

Examples of local anesthetics include dibucaine hydrochloride, dibucaine, lidocaine hydrochloride, lidocaine, benzocaine, pramoxine hydrochloride, tetracaine, tetracaine hydrochloride, oxyprocaine hydrochloride, mepivacaine, piperocaine hydrochloride, etc.

Examples of skin moisturizer ingredients include the three categories of humectants, emollients and preservatives. Humectants, such as urea, glycerin and alpha hydroxy acids, help absorb moisture from the air and hold it in the skin. Emollients, such as lanolin, mineral oil and petrolatum, help fill in spaces between skin cells, lubricating and smoothing the skin. Preservatives help prevent bacteria growth in moisturizers. Other ingredients that moisturizers may contain include vitamins, minerals, plant extracts and fragrances.

Examples of antibiotics include neomycin, erythromycin, and the anti-viral agent docosanol (Abreva®), and experimental agents such as N,N-dichloro-dimethyltaurine. Topical anti-acne agents include benzoyl peroxide, resorcinol, resorcinol monoacetate, and salicylic acid. Other agents to counter acne include topical retinoids such as adapalene and isotretinoin (Retin-A, Differen, and Tazorac). Examples of keratolytics include such agents as, alpha-hydroxy acids, glycolic acid, and salicylic acid.

The adjunct DIPA compound can be used for medications that are useful for human therapy as well as for veterinarian uses.

Study 1

Toxicity

Preliminary toxicological studies were conducted on DIPA 1-7. It was not mutagenic in the Ames test (Strains TA 98 and TA100, with and without liver activation) (tests conducted by Apredica, Watertown, Mass., USA).

DIPA-1-7, dissolved in 3% ethanol/97% 1,2-propanediol, or vehicle alone, was administered at 20 mg/kg perioral for 7 days (N=10 per group) to male rats, and on the 8th day, the animals were euthanized with sodium pentobarbital and the major organs (body, heart, liver, lungs, kidney, testes, brain) were removed and weighed. Heart tissues (ventricle and heart valves) and liver samples were stained with hematoxylin and eosin and the histology examined. There was no significant difference in body or organ weights between the two groups and the heart and liver histology were normal.

Study 2
Tissue Temperature

The compounds of the present discovery simulate the sensations of heat abstraction, but do not alter tissue temperatures. The average forehead skin temperature of subjects (N=5) was measured following application of DIPA-1-7 (with a wipe at a concentration of 20 mg/mL in distilled water) to the forehead skin. The results are summarized in Table 5. The subjects noted the cooling effect of DIPA-1-7 on the skin which lasted for 30-45 minutes; however, skin temperatures were not affected.

TABLE 5

Skin temperatures of human forehead after DIPA-1-7, 20 mg/mL.

| | Temperature (° C.) | |
|---|---|---|
| Time | Control | DIPA-1-7 |
| Before | 37.3 | 37.4 |
| 0 minutes | 37.2 | 37.4 |
| 15 minutes | 37.5 | 37.5 |
| 30 minutes | 37.1 | 37.1 |
| 45 minutes | 37.4 | 37.2 |
| 60 minutes | 37.0 | 37.1 |

Study 3
Sensory Effects of Compounds on Facial Skin

When a test compound is applied to the skin, it is possible to characterize the resulting sensations. The quality of the sensations produced by individual compounds favours certain characteristics that are distinct. The quality of the sensations evoked, their descriptors, and their proposed mechanism of action, are summarised in Table 6. For any compound, there may be some overlap in activity, but usually one compound occupies only one or two categories of sensations. For example, icilin is exclusively cool, with very little "cold". DIPA-1-6 and DIPA-1-7 are exceptional in producing pleasant, robust "dynamic cool." DIPA-1-8, 2-6, are 2-7 are strong cold-producing agents.

TABLE 6

Descriptor and proposed mechanisms of DIPA compounds on skin.

| Type of Sensation | Descriptor | Proposed Mechanisms on Sensory Neurons |
|---|---|---|
| Inactive | No effect | — |
| Cool, steady and pleasant | Cool | Balanced stimulation of static and dynamic |
| Cold, constant, but limited by desensitization | Cold | Higher stimulation of static |
| Dynamic cooling, robust cool/cold, strong refreshing | Dynamic cool | Higher stimulation of dynamic |
| Stinging cold, sometimes with irritation | Icy cold | Stimulation of dynamic and static, and also nociceptive sites |

Even after the offset of the cooling/cold action, some of the compounds have a "reservoir effect." Experimentally, this is measured 1 hour after offset by placing a hot and then a cold towel over the site of application and determining if the onset of cooling/cold returns for at least 30 minutes. If this occurs, then there is a positive "reservoir effect". The "reservoir effect" can also be provoked with air movement, but the conditions for air movement are difficult to standardize. The "reservoir effect" of DIPA-compounds in skin is most likely due to residual drug that is reactivated to stimulate dynamic/static sensory neurons.

In the studies described herein, the sensation of coolness/cold is rated as 0, 1, 2, or 3 with: 0 as no change; 1 as slight coolness, or cold; 2 as clear-cut signal of coolness or cold; and 3 as strong cooling or cold. The sensations are recorded at intervals of 5 to 15 minutes, until at least two successive zeroes are obtained.

The onset of drug action is taken as the time to reach 2 units of coolness intensity.

The duration of sensory action is defined as the offset time minus the onset time. The offset of drug action is defined here as the time when coolness intensity drops below 2, after previously surpassing 2 units. An inactive compound is defined as one that does not exceed 2 units of cooling for 5 minutes or more after application. The offset endpoint is sometimes unstable for compounds that act for two or more hours, because the coolness/cold sensation may fluctuate due to environmental variables such as sunlight, ventilation, activity, and the "reservoir effect." For example, DIPA-1-8 and 2-8 are exceptionally long-acting on the skin.

The effects of test compounds on periorbital skin, malar (zygomatic) skin, and forehead skin were determined.

Compounds were tested on periorbital skin. Test compounds were applied to the closed eyelids using cotton gauze (0.4 g, rectangular, 50 mm×60 mm; from CS-being, Daisan Cotton, Japan). The test compounds were used at a concentration of 1 mg/mL in distilled water. The duration of the sensory effect was measured with a stopwatch. The degree of "dynamic cool" was graded from 0 to +++, with intermediate steps of + and ++. An anti-fatigue effect was present only if there was sufficient "dynamic cool."

The results are summarized in Table 7.

TABLE 7

Sensory effects after application to periorbital skin.

| Code | $R_3$ | Carbon atoms | Sensory Quality | Anti-fatigue | Duration (hr) | Sting on Ocular Surface |
|---|---|---|---|---|---|---|
| DIPA-1-5 | 5 | 11 | dynamic | + | 0.5 | No |
| DIPA-1-6 | 6 | 12 | dynamic | ++ | 3.8 | Yes |
| DIPA-1-7 | 7 | 13 | dynamic | +++ | 4.2 | No |
| DIPA-1-8 | 8 | 14 | cool | ++ | 2.1 | No |
| DIPA-1-9 | 9 | 15 | cool | 0 | 3.0 | No |
| 2-4 | 4 | 12 | cool | 0 | 0.1 | No |
| 2-5 | 5 | 13 | cool | + | 2.1 | No |
| 2-6 | 6 | 14 | cool | ++ | 6.2 | Yes |
| 2-7 | 7 | 15 | cool | + | 1.2 | Yes |
| 2-8 | 8 | 16 | cool | + | 1.3 | No |

Compounds were tested on zygomatic and forehead skin. Test compounds were applied to the skin of the forehead and zygomatic using cotton gauze (0.4 g, rectangular, 50 mm×60 mm; from CS-being, Daisan Cotton, Japan). The test compounds were used at a concentration of 20 mg/mL in distilled water. The onset and duration of the sensory effect was measured with a stopwatch. The degree of "dynamic cool" was graded from 0 to +++, with intermediate steps of + and ++. An anti-fatigue effect was present only if there was sufficient "dynamic cool."

The results are summarized in the Table 8.

TABLE 8

Sensory effects after application to zygomatic and forehead skin.

| Code | $R_3$ | Carbon atoms | Onset (min) | Sensory Quality | Anti-Fatigue | Duration (hr) | Reservoir Effect |
|---|---|---|---|---|---|---|---|
| DIPA-1-5 | 5 | 11 | ~1 | dynamic | 0 | 0.5 | No |
| DIPA-1-6 | 6 | 12 | ~1 | dynamic | ++ | 1.3 | Yes |
| DIPA-1-7 | 7 | 13 | ~1 | dynamic-icy | +++ | 3.2 | Yes |
| DIPA-1-8 | 8 | 14 | ~1 | cold-icy | ++ | 4.0 | Yes |
| DIPA-1-9 | 9 | 15 | ~2 | cool | 0 | 2.0 | No |
| 2-4 | 4 | 12 | ~1 | cool | 0 | 0.3 | No |
| 2-5 | 5 | 13 | ~1 | cool | 0 | 1.1 | Yes |
| 2-6 | 6 | 14 | ~2 | cold | + | 1.5 | Yes |
| 2-7 | 7 | 15 | ~2 | cold | + | 2.4 | Yes |
| 2-8 | 8 | 16 | 5 | cold | 0 | 5.6 | Yes |

Each of 3-1 and 3-2 was tested and found to be inactive on periorbital, and zygomatic/forehead skin.

Notably, DIPA-1-7 selectively produced the unusual sensation of "dynamic cool" and also had anti-fatigue effects. From the data shown above, it can be seen that, among these compounds, DIPA-1-7 evoked "dynamic cool" on both periorbital and zygomatic/forehead surface. Another compound with similar properties was DIPA-1-8, but this compound is was more cold/icy cold, although it had the desirable property of a longer duration of action on the zygomatic/forehead surface. The long duration of action of DIPA-1-7 and DIPA-1-8 on the skin adds value as an anti-fatigue agent, especially for the fatigue of chronic illness. As shown in the case studies described below, a single application of DIPA-1-7 is sufficient to counteract fatigue and heat stress for at least three to four hours.

A special value of DIPA-1-9 is the comfortable cooling it provides and its long duration of action after periorbital application, and the absence of any stinging. Thus, it has a special therapeutic niche for the relief of ocular discomfort.

A study of structure-activity relationships did not reveal any attributes of DIPA-1-7 that would have predicted its unique properties. For example, dynamic cool is seen with comparative compound 2-5 on the oropharyngeal surface, but 2-5 does not elicit this sensation when applied the skin with a wipe. The comparative 2-6 and 2-7 analogs have similar properties to embodiment DIPA-1-7 but have undesirable strong "reservoir effects" especially when used near the ocular rim.

The sensory properties of the anti-fatigue effects of DIPA compounds and their duration of action could not have been predicted based on standard correlations of lipophilic and hydrophilic parameters. For the duration of action on the zygomatic/forehead skin, increasing the number of carbons on $R_3$ increased the duration of cooling, as might be predicted on the basis of lipophilicity, but the periorbital effects indicate hydrophilicity is also important for anti-fatigue actions. In the section on "Receptor Mechanisms", the importance of a partial charge on the phosphinoyl oxygen for hydrogen bonding and an "on-off" or "rapid association-dissociation" for activating dynamic cool are discussed. The results here for the selective attributes of DIPA-1-7 and DIPA-1-8 are unexpected, surprising, and has practical applications for counter-acting fatigue and anti-nociception.

Study 4
Agonist Activity of Compounds on TRPM8

The in vitro effects of test compounds were evaluated on cloned hTRPM8 channel (encoded by the human TRPM8 gene, expressed in CHO cells) using a Fluo-8 calcium kit and a Fluorescence Imaging Plate Reader (FLIPRTETRA$^{TETRA}$™) instrument. The assays were conducted by ChanTest Corporation (14656 Neo Parkway, Cleveland, Ohio 44128, USA).

Test compounds and positive control solutions were prepared by diluting stock solutions in a HEPES-buffered physiological saline (HBPS) solution. The test compound and control formulations were loaded in polypropylene or glass-lined 384-well plates, and placed into the FLIPR instrument (Molecular Devices Corporation, Union City, Calif., USA). The test compounds were evaluated at 4 or 8 concentrations with n=4 replicates per determination. The positive control reference compound was L-menthol, a known TRPM8 agonist. The test cells were Chinese Hamster Ovary (CHO) cells stably transfected with human TRPM8 cDNAs.

For FLIPR$^{TETRA}$™ assay, cells were plated in 384-well black wall, flat clear-bottom microtiter plates (Type: BD Biocoat Poly-D-Lysine Multiwell Cell Culture Plate) at approximately 30,000 cells per well. Cells were incubated at 37° C. overnight to reach a near confluent monolayer appropriate for use in a fluorescence assay. The test procedure was to remove the growth media and to add 40 µL of HBPS containing Fluo-8 for 30 minutes at 37° C. 10 µL of test compound, vehicle, or control solutions in HBPS were added to each well and read for 4 minutes.
0.7
Concentration-response data were analyzed via the FLIPR Control software that is supplied with the FLIPR System (MDS-AT) and fitted to a Hill equation of the following form:

$$\text{RESPONSE} = \text{Base} + \frac{\text{Max} - \text{Base}}{1 + \left(\frac{\text{xhalf}}{x}\right)^{rate}}$$

where: "Base" is the response at low concentrations of test compound; "Max" is the maximum response at high concentrations; "xhalf" is the $EC_{50}$, the concentration of test compound producing half-maximal activation; and "rate" is the Hill coefficient. Nonlinear least squares fits were made assuming a simple one-to-one binding model. The 95% Confidence Interval was obtained using the GraphPad Prism 6 software.

The results are summarized in Table 9.

TABLE 9

$EC_{50}$ and relative potency of compounds on TRPM8 . . .

| Code | $EC_{50}$ µM | 95% Confidence Interval | Relative Potency |
|---|---|---|---|
| Menthol | 3.8 | 2.5 to 5.6 | 1.0 |
| DIPA-1-5 | 5.6 | 4.4 to 7.2 | 0.7 |
| DIPA-1-6 | 2.4 | 1.5 to 4.0 | 1.6 |
| DIPA-1-7 | 0.7 | 0.5 to 1.0 | 5.4 |
| DIPA-1-8 | 0.7 | 0.5 to 1.0 | 5.4 |
| DIPA-1-9 | 0.9 | 0.4 to 2.5 | 4.0 |
| 2-4 | 14.5 | 7 to 29 | 0.3 |
| 2-5 | 1.7 | 1.0 to 2.9 | 2.2 |
| 2-6 | 0.8 | 0.5 to 1.3 | 4.7 |
| 2-7 | 1.1 | 0.6 to 2.3 | 3.4 |
| 2-8 | 1.3 | 0.7 to 2.3 | 2.9 |
| 3-1 | 24 | 8 to 76 | 0.2 |
| 3-2 | 4.2 | 1.6 to 10.8 | 0.9 |

Of the 12 compounds tested, all showed full efficacy on the TRPM8 receptor, i.e., at higher tested concentrations there was ~100% stimulation of calcium entry, and the data fitted a sigmoidal dose-response curve. The results for the "di-isopropyl" compounds of this invention are illustrated in FIG. 3.

Figure 3:
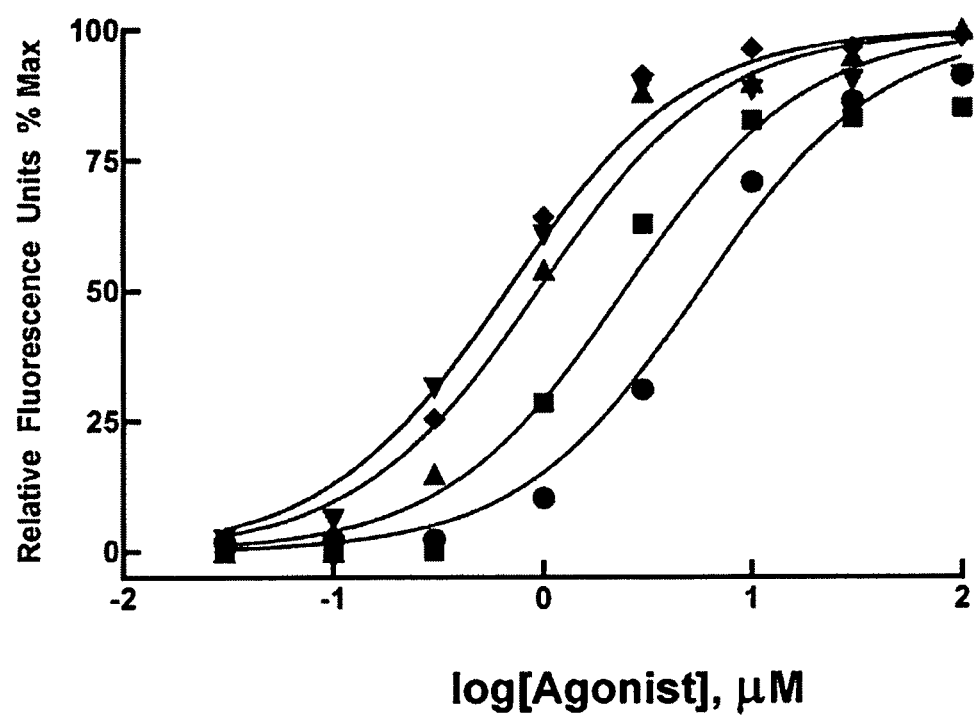
FIG. 3 is a graph of response (Relative Fluorescence Units; % of maximum) as a function of the logarithm of the concentration of the test compound (denoted agonist), expressed in μM, for each of embodiments of the invention: DIPA-1-5 (circles), DIPA-1-6 (squares), DIPA-1-7 (inverted triangle), DIPA-1-8 (diamonds), or DIPA-1-9 (up-right triangle).

FIG. 3 is a graph of response (Relative Fluorescence Units; % of maximum) as a function of the logarithm of the concentration of the test compound (denoted agonist), expressed in µM, for each of DIPA-1-5 (circles), DIPA-1-6 (squares), DIPA-1-7 (inverted triangle), DIPA-1-8 (diamonds), or DIPA-1-9 (up-right triangle).

The $EC_{50}$ of the more potent compounds (DIPA-1-7, DIPA-1-8, DIPA-1-9, 2-5, 2-6, 2-7, 2-8) fell within a narrow range with overlapping 95% Confidence Intervals. The potency of DIPA-1-7 and DIPA-1-8 are similar and significantly greater than the potencies of DIPA-1-5 and DIPA-1-6. By contrast the structural modifications of comparative compounds 3-1 and 3-2 resulted in a significant loss of bioactivity To examine the specificity of the test compounds, further studies were conducted on TRPV1 channels (human TRPV1 gene expressed in HEK293 cells) and TRPA1 channels (human TRPA1 gene expressed in CHO cells). The test cells were Chinese Hamster Ovary (CHO) cells or Human Embyronic Kidney (HEK) 293 cells transfected with human TRPV1 or TRPA1 cDNAs. The positive control reference compound was capsaicin (a known TRPV1 agonist) or mustard oil (a known TRPA1 agonist). DIPA-1-7 and DIPA-1-8 did not exhibit any agonist on antagonist activity on TRPA1 channels at maximum tested concentrations of 100 µM. A weak TRPV1 agonist activity was found for DIPA-1-7, but this was not dose-dependent.

In bioactivity studies, potency was not correlated to the TRPM8 $EC_{50}$. For example, DIPA-1-5 and 1-6 are more potent in producing shaking behavior than 1-7 and 1-8 [see Study 6]. Also, DIPA-1-7 is more effective at producing the sensation of "dynamic cool" on the skin and on the ocular surface. There were no distinguishing features in the $EC_{50}$ data which enabled prediction of which compounds have potent "dynamic cool" properties. Thus, $EC_{50}$ values do not give information on the quality of the heat abstraction sensation, the duration of action, or the accessibility of the molecule to tissue targets. The identification of selective agents requires bioassays that more directly address these questions.

Study 5
Studies on Isolated Vagus Nerve: Direct Anti-Nociceptive Activity

To determine if DIPA-1-7 acted directly on sensory nerves, it was tested in an isolated nerve model developed at the Imperial College, London, U.K. [Birrell et al. TrpA1 agonists evoke coughing in guinea pig and human volunteers. Amer. J. respiratory and critical care medicine 180, 1042-7, 2009; Patel, H. J. et al. Inhibition of guinea-pig and human sensory nerve activity and the cough reflex in guineapigs by cannabinoid (CB2) receptor activation. Brit. J. Pharmacol. 140, 261-8, 2003]. In this in vitro assay, segments of the mouse vagus nerve are placed on a platform and the electrical activity is recorded after topical application of capsaicin. Capsaicin is a known irritant that elicits pain when it is applied to the skin and it will depolarize the isolated vagus. The ability of substances to inhibit this capsaicin-induced depolarization is measured.

Briefly, segments of vagus nerve, caudal to the nodose ganglion, were removed from mice with fine forceps and segments placed in oxygenated Krebs solution and bubbled with 95% $O_2$/5% $CO_2$. The desheathed nerve trunk was mounted in a 'grease-gap' recording chamber and constantly superfused with Krebs solution with a flow rate of approximately 2 mL/min, and the electrical activity of the nerve monitored with electrodes. The temperature of the perfusate was kept constant at 37° C. by a water bath. Nerve depolarizations were induced by superfusion of the nerve with capsaicin (1 µM). After two reproducible depolarization responses to capsaicin, DIPA-1-7 was applied at 1 mg/mL (4 µM) for 10 minutes in the perfusate followed by capsaicin. The nerves were then washed with Krebs until the responses had returned to baseline and challenged again with capsaicin. The results and tracings obtained in normal and TRPM8 knockout mouse are shown in FIG. 4.

Figure 4:
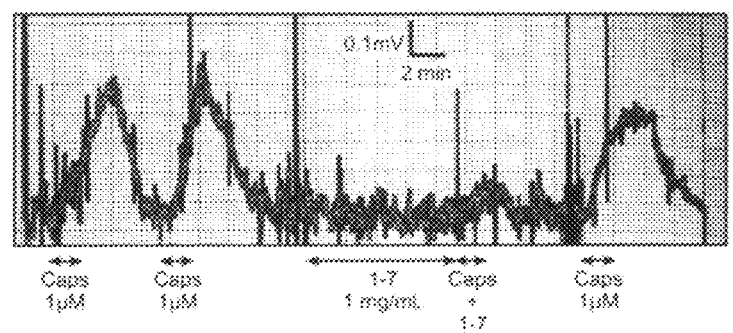
FIG. 4 shows chart traces that illustrate, in the first trace (FIG. 4A "Wild Type"), the inhibition of capsaicin-induced depolarization of the isolated mouse vagus by the DIPA-1-7 embodiment, superfused at a concentration of 1 mg/mL, and, in the second trace (FIG. 4B "TRPM8 KO"), the significant absence of inhibition in the isolated TRPM8 KO (knockout) mouse vagus by DIPA-1-7, superfused at a concentration of 1 mg/mL.
Figure 4:
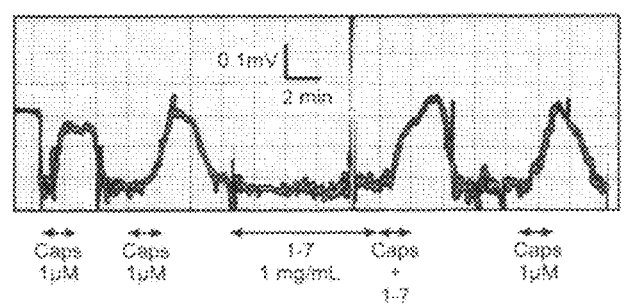

FIG. 4 shows chart traces that illustrate, in the first trace ("Wild Type"), the inhibition of capsaicin-induced depolarization of the isolated mouse vagus by DIPA-1-7, superfused at a concentration of 1 mg/mL, and, in the second trace ("TRPM8 KO"), the significant absence of inhibition in the isolated TRPM8 KO (knockout) mouse vagus by DIPA-1-7, superfused at a concentration of 1 mg/mL.

In the tracings shown in the FIG. 4, the first two peaks show the depolarization response of the mouse vagus to capsaicin ("Caps"). After DIPA-1-7 is applied (1 mg/mL), the response is suppressed in the normal mouse vagus ("Wild Type"), but not in the TRPM8 knock-out ("TRPM8 KO") mouse vagus.

The percent inhibition of capsaicin-induced depolarization of the isolated normal mouse vagus caused by DIPA-1-7 was about 75%; the percent inhibition of capsaicin-induced depolarization of the isolated TRPM8 knock-out mouse vagus caused by DIPA-1-7 was about 20%.

This experiment clearly demonstrates a direct pharmacological action of the DIPA-1-7 on the sensory nerve, which is a surprising and unexpected result. Furthermore, the diminished response in the TRPM8 KO mouse indicated that the receptor target was TRPM8. These results provide strong evidence that DIPA-1-7 can be used as an anti-nociceptive agent and the target receptor is TRPM8.

Capsaicin is a TRPV1 agonist and the search for an effective TRPV1 antagonist has been the super-intense quest of many pharmaceutical companies for the past ten or more year. Here, it is shown that DIPA-1-7 is an effective "physiological" antagonist of TRPV1 at low concentrations. DIPA-1-7, by itself, did not evoke depolarization, indicating that it is free of agonist activity at this "pain" receptor. These results strongly indicate the usefulness of DIPA-1-7 as an anti-nociceptive agent.

Study 6
Activity in Laboratory Rat: Perioral and Topical Delivery

Fur-coated and feathered animals—when wet and cold—shake, like a wet dog (see, e.g., Dickerson et al., 2012; Ortega-Jimenez et al., 2012; Wei, 1981). These shakes are rapid alternating contractions of the supination and pronation muscles about the spinal axis, and can be readily observed and counted. "Wet-dog shaking" has been studied in detail in animals and this behaviour is interpreted to have survival value because shaking, by removing the water off t skin, reduces the need to expend evaporative energy to remove wetness. The triggering sensation for shaking is thus having water trapped in between hair follicles or feathers. Humans have little hair on skin and do not shake. The likely equivalent behaviour to shaking in humans is shivering, a condition caused by generalized sensations of coolness/cold and wetness.

Drug-induced shaking in animals has been reviewed (see, e.g., Wei, 1981). Under the right conditions, drug-induced shaking can be observed in the pentobarbital-anesthetized rat, enhanced by hypothermia and cold, and inhibited by elevating body temperature.

Test compounds were evaluated for "wet-dog shaking" as a model of dynamic cooling. Using a standardized procedure, test compounds were compared in their ability to stimulate the shaking response by perioral administration and by topical delivery to the abdominal skin.

Perioral. Test compounds were dissolved in saline and administered by oral gavage to pentobarbital-anesthetized male albino rats at 20 mg/kg at a volume of 0.1 mL/100 g body weight [N=3 to 4 rats per compound]. Shaking was counted over a 40 min period and recorded at 10-min intervals.

Three of the four "di-isopropyl" compounds caused vigorous shaking. The "di-secbutyl" compounds were relatively inactive, except 2-5 which elicited an average of 4 shakes in the 40 min observation period. By contrast, DIPA-1-5, DIPA-1-6, and DIPA-1-7 produced an average shaking frequency of 86, 56, and 36 shakes, respectively. The strong activity of DIPA-1-5 was unusual. Applied to the skin, DIPA-1-5 has a refreshing "dynamic cool", but the duration of action of only about 30 min was significantly less than that for DIPA-1-6 and DIPA-1-7. The shorter duration of action of DIPA-1-5 limits its practical utility. It is possible that its smaller molecular size facilitates absorption and allows greater access to systemic receptors, and therefore more shaking.

The relationship of the shake response to temperature sensation was further studied [in pentobarbital-anesthetized rats]. After injection of the anaesthetic, rectal temperature drops, and reaches approximately 35° C. in about 10 min. This hypothermia can be reversed by placing the animal on a heated surface and body temperature maintained at 38° C. DIPA-1-7 20 mg/kg perioral elicited 36±5 shakes (N=6) in the anesthetized rat, but in the heated animals, the shaking frequency was significantly reduced to 5±2 shakes (N=6) [P<0.001]. The reduction of shaking frequency by ⅔ under heat indicated that the shake response was linked to cold sensations and shivering.

Topical. Shaking is an excellent indicator of in vivo effect. Methods were developed. to determine if shaking was seen after topical application of DIPA compounds. The abdominal skin of the pentobarbital-anesthetized rat was shaved and 20 μL of the pure unadulterated DIPA chemical was applied with a micropipette on a ~1 cm diameter circle of skin, enclosed with a ring of cream [Baby cream "Nevskaya kosmetika Detskyi" Nevskaya Kosmetika Inc., Saint-Petrsburg 192029], as shown in the FIG. 4. The number of shakes was counted for 1 hr after application.

Figure 5:
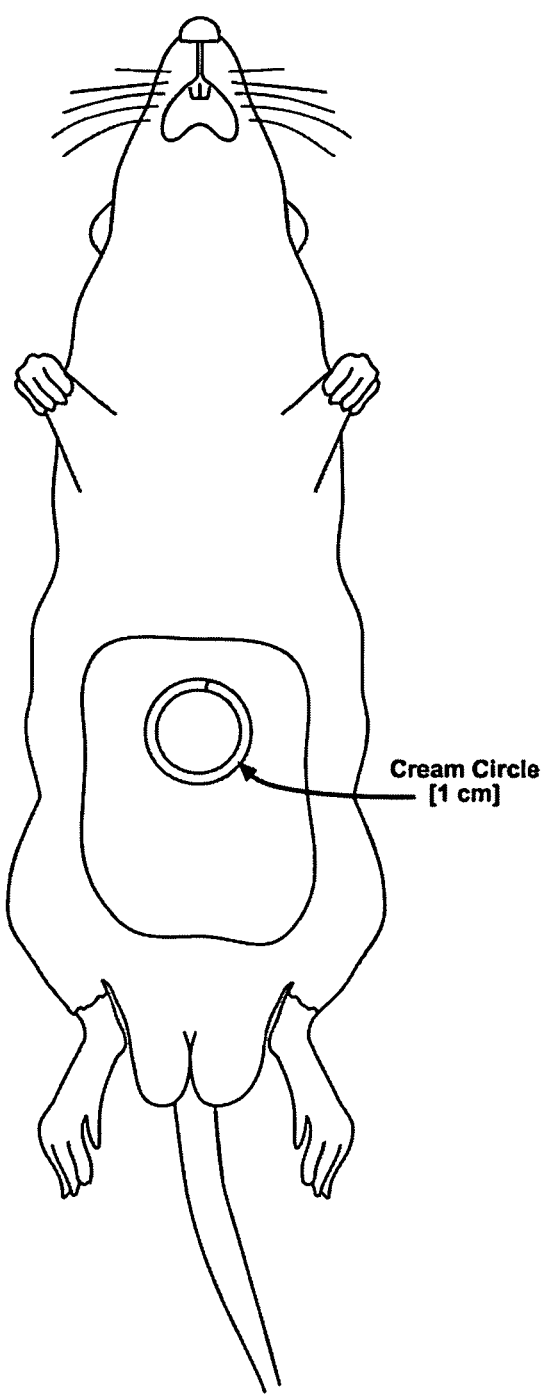
FIG. 5 shows the method for measuring the transdermal activity of the DIPA-embodiment compounds applied 20 μL with a micropipette to the center of a circle enclosed by cream on the abdominal skin of an anesthetized rat. Shaking frequency was counted for 1 hr after topical application.

FIG. 5 shows the method for measuring the transdermal activity of DIPA-compounds applied 20 μL with a micropipette to the center of a circle enclosed by cream on the abdominal skin of an anesthetized rat. Shaking frequency was counted for 1 hr after topical application. The data and results for topical for perioral responses are summarized in the Table 10. The data are further plotted graphically in FIG. 6, to show the lack of correlation of TRPM8 potency to in vivo bioactivity.

Figure 6:
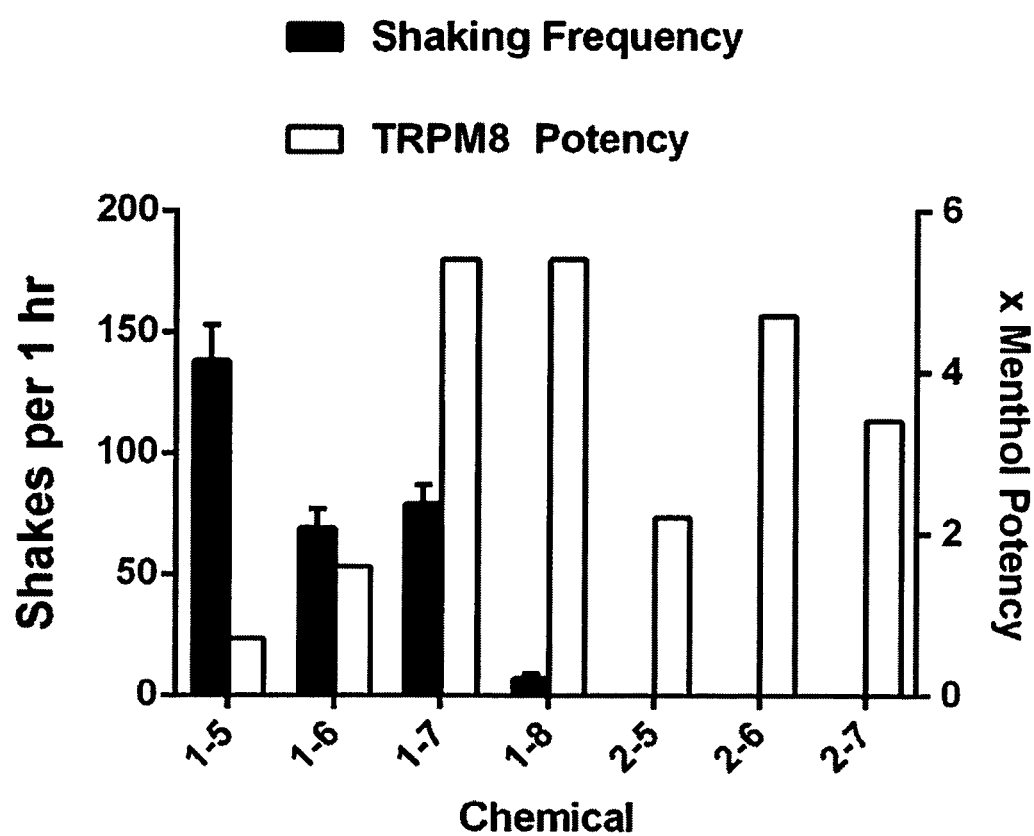
FIG. 6 shows shaking frequency [black bars, left ordinate] after transdermal application and the lack of correlation to TRPM8 potency [right ordinate, inverse of $EC_{50}$, potency relative to menthol] for test chemicals. It can be seen that the embodiments DIPA-1-5, DIPA-1-6, and DIPA-1-7 readily evoke robust shaking, but this is not seen with the other analogs.

The data in Table 10 and FIG. 6 provide the STRONGEST evidence for the novelty and exceptional properties for the compounds of this discovery. It is clear that these compounds penetrate biological membranes and rapidly evoke responses; events that are not seen with the comparative di-sec-butyl analogs. Furthermore, the bioactivity is not correlated to the potency measurement [$EC_{50}$] on the TRPM8 receptor. This is the first time that shaking responses of such magnitude have been shown after topical [dermal] application of a chemical.

TABLE 10

Shaking frequency after perioral [per 20 mg/kg body weight] or topical delivery of 20 μl test compounds [per animal] to the anesthetized rat.

| Code | Mol Wt | # Cs | Sensation | Perioral | Topical | xMenthol |
|---|---|---|---|---|---|---|
| DIPA-1-5 | 204 | 11 | dynamic cool | 86 ± 7 | 138 ± 15 | 0.7 |
| DIPA-1-6 | 218 | 12 | dynamic cool | 56 ± 5 | 69 ± 8 | 1.6 |
| DIPA-1-7 | 232 | 13 | dynamic cool | 36 ± 4 | 79 ± 8 | 5.4 |
| DIPA-1-8 | 246 | 14 | cool | 0 | 7 ± 2 | 5.4 |
| DIPA-1-9 | 260 | 15 | mild cool | 0 | 0 | 4.0 |
| 2-4 | 218 | 12 | cool | 0 | 0 | 0.3 |
| 2-5 | 232 | 13 | cool | 4 ± 1 | 0 | 2.2 |
| 2-6 | 246 | 14 | cool | 0 | 0 | 4.7 |
| 2-7 | 260 | 15 | cool | 0 | 0 | 3.4 |
| 2-8 | 274 | 16 | cool | 0 | 0 | 2.9 |

Surprisingly, vigorous shaking was evoked with inventive embodiments DIPA-1-5, DIPA-1-6, and DIPA-1-7. Only a weak response was seen with DIPA-1-8, and the comparative di-sec-butyl analogs, 2-5, 2-6, and 2-7, were inactive. The shaking induced by DIPA-1-7 was dose-dependent. Topical application of 5 μl, 10 μl, 20 μl, or 50 μl of DIPA-1-7 elicited an average of 25±3, 53±6, 79±8 and 118±12 shakes, respectively, in 1 hr. Shaking was seen if DIPA-1-7 was diluted 50-50 with either water or saline (at the 10 μl dose), but it was completely inhibited if 50% (R)-1,2-propanediol was added to the DIPA-1-7 (at the 10 μl dose) as a diluent. This surprising result shows that DIPA-1-7 penetrates the skin in aqueous solution. This facile permeability of DIPA-1-7 is reminiscent of menthol, and suggests DIPA-1-7 is easily delivered into the dermis by topical application. Furthermore, DIPA-1-7 may be used to penetrate thick keratotic skin lesions, for example in psoriasis or in contact dermatits of the hands, to alleviate itch and pain. The adjustment of DIPA-1-7 concentrations in polyhydric solvent such as 1,2-propanediol can be used to control the degree of absorption of DIPA-1-7, an art well-known to formulation experts.

The surprising potency of DIPA-1-5 and DIPA-1-6 was unexpected. These molecules work for a shorter time on skin cooling than DIPA1-7. These smaller may penetrate faster through the skin barrier and go into the systemic circulation. However, the value of this fast action is uncertain. In most contemplated topical applications of this discovery, the preference is for the drug action to remain localized and not systemic.

When the relative activities of the analogs for producing shaking are compared to the $EC_{50}$ for TRPM8 activation, it can be seen that the two variables are not correlated. The limitations of the TRPM8 $EC_{50}$ for predicting bioactivity were discussed on page 62.

The results here provide the strongest objective laboratory evidence that the DIPA compounds of Formula 1 selectively produce vigorous "dynamic cool". The total number of carbons, or the number of carbons in the largest alkyl group, did not correlate to the magnitude of bioactivity.

Study 7

Effects on Topical Sites on the Cranium

DIPA-1-7, the most potent compound for dynamic cooling, was tested at other topical sites on the cranium. A 20 mg/mL solution was applied, using a cotton wipe, onto the skin above the buccal cheek, the parotid-masseteric cheek, temple, and the skin above the periauricular region, and the posterior mandible using the appropriate craniometric points (pterion, coronion, condylion, and gonion, respectively) as landmarks. Surprisingly, at all of these sites, other than the buccal cheek, little cooling, if any, was observed. Mild cooling was observed on the buccal cheek for approximately 30 minutes, but this effect may have been due to the spread of the solution onto the receptive field of the infraorbital nerve. Thus, the action on orbit and zygomatic/forehead skin is selective and identifies the important delivery targets on the skin of the head.

The head is known to be a site where cooling helps relieve heat discomfort. In a study described in Nakamura et al. [2012], eleven male subjects were exposed to mild heat. Subjects, clothed in only short pants, entered a climatic chamber maintained at 32.5±0.5° C. with a relative humidity of 50%. About 1.5 hours after entry into the chamber, a local cooling protocol was initiated with water-perfused stimulators placed on the head, chest, abdomen, or thigh. Cooling of the face and thigh was felt by the subjects to be more effective than cooling of the chest and abdomen in reducing the heat discomfort.

In a study described by Essick et al. [Site-dependent and subject-related variations in perioral thermal sensitivity. Somatosensory & motor research 21, 159-75, 2004] the thresholds for detection of cooling and cold pain on various sites of the face, ventral forearm, and scalp was determined for 34 young adults. The most sensitive sites were on the vermilion which could detect a temperature change of about 0.5° C., followed by areas around the mouth (upper and lower hairy lip, mouth corner) and lateral chin. The midcheek and periauricular skin were less sensitive (able to detect a temperature change of about 2° C.), and the forearm and scalp were least sensitive (able to detect a temperature change of about 3° C.). The sensitivities of the orbital, zygomatic and forehead skin were not tested.

Use of DIPA-1-7 on the orbital and zygomatic/forehead skin, for example, in an office environment or in heat stress, may be inconvenient if the subjects uses cosmetic make-up at these sites. Surprisingly, it was found that DIPA-1-7, at 20 mg/mL, can produce a dynamic cooling effect when applied on the scalp, especially near the hairline. This effect is sufficient to counter fatigue caused by heat. Likewise, rubbing DIPA-1-7 on the skin in the centre of the chest, above the sternum, can counteract the discomforts of heat. At these application sites, cosmetics are not affected, yet an invigorating coolness, that counteracts the debilitating effect of heat, is achieved.

The ability of DIPA-1-7 to cause cooling of the scalp and hairline is also important for treating itch at these sites in conditions such as psoriasis, dandruff, and seborrheic dermatitis.

Case Studies

Case studies are described below which demonstrate the use of DIPA-1-7: (a) to enhance cognition, decrease mental lassitude and fatigue, and to energize performance; (b) to counteract tiredness and fatigue from chronic illness; (c) to counteract the fatigue and/or discomfort from heat stress; (d) to counteract skin itch and pain, and (e) to reduce the severity of "night sweats".

In these studies, subjects were given dosages units containing 1.5 to 1.75 mL of DIPA-1-7 stored in 2.0 mL microcentrifuge tubes (Nova Biostorage Plus, Canonsburg, Pa. 15317) and cotton gauze (0.4 g, rectangular, 50 mm×60 mml; from CS-being, Daisan Cotton, Japan). The DIPA-1-7 was provided as a solution in distilled water or 2% ethanol-98% distilled water, at a DIPA-1-7 concentration of 1 mg/mL or 5 mg/mL. The subjects were given instructions on how to place the solution on the gauze and how to wipe the wet gauze over the skin surfaces with the eyes closed: 5 mg/mL for the orbital and zygomatic/forehead skin, away from the palpebral sulcus, and 1 mg/mL if the primary site was the periorbital skin. Approximately 0.35 mL and 0.15 mL are delivered by these methods of application, respectively.

For some test (comparative) compounds (e.g., 2-6 and 2-7), residues that remain on orbital skin can enter the ocular surface and cause stinging and discomfort when a subject sweats or takes a shower. This problem was minimal with inventive embodiments DIPA-1-7 and DIPA-1-8. Subjects were instructed to rinse with water or a wet towel any surfaces that become irritable; however, irritation and discomfort was rarely seen with DIPA-1-7 or DIPA-1-8 at these concentrations.

Case Study 1

A 65-year old male is an avid snooker player and likes to frequent the snooker parlours of London and Hong Kong. He plays for small wagers with his friends, but with advancing age his game has deteriorated and he can only play about eight frames in one day. He uses ice-cold towels on his face and prescription glasses to help him during games, but feels that it is the lack of concentration and the planning of sequences of shots that hinders his game and prevents him from completing "breaks" (a continuous accumulation of points in a "run"). He volunteered to try wipes containing DIPA-1-7. There was a remarkable transformation in his game. He moved faster from shot to shot and the planning and execution was crisp. The number of frames per session increased as well as his frequency of play. He had his longest career break of 80 points and was ecstatic. He continues to use the wipes as an aid to his snooker game. He also noted that enhancement of his cognitive facilities could be renewed and invigorated by applying the ice cold towel to his face (an example of the "reservoir effect"). He noted, however, it was important to avoid excessive entry of the DIPA-1-7 onto his ocular surface because that sometimes caused irritation, especially if the use was too frequent. With practice, he noted that cognitive enhancement of his game could be regulated and controlled by optimizing the delivery procedures.

A 70-year old retired architect likes to play penny poker once or twice a week with his buddies. He volunteered to try wipes containing 5 mg/mL of DIPA-1-7 to see if it would improve his poker skills. He did this at first without telling his friends. He immediately noticed after application of the wipe that he was more awake than the other players. He could remember the cards that were discarded, could calculate and remember the odds of various hands (e.g., likelihood of drawing successfully to a four-card two-way straight or a four-card flush), but most importantly, he could also sense if his opponent had a strong or weak hand, and if they were bluffing. He felt energized, more adventurous, and willing to take risks by bluffing himself. He made decisions quickly and with more confidence. He felt that his game was more insightful and improved. He felt guilty about having an unfair advantage over his friends and encouraged several of the other players to try the wipes. All noticed the invigorating dynamic cool sensations but they were less sure if their poker skills were improved.

A 68-year old pharmacologist spends his time in research and in the design and management of clinical trials. He owns his consulting firm with eight employees, and spends at least 8 to 12 hours per day in front of a computer monitor. He has in his working space an espresso machine, and boxes of cigarettes and cigars. He uses coffee and tobacco to sharpen his thinking. He agreed to apply the wipes containing DIPA-1-7 at 1 mg/mL (periorbital only) and 5 mg/mL (periorbital and zygomatic/forehead) and noted that his tiredness went away for at least 6 to 8 hours and that he was able to concentrate and think more clearly. He said the wipes were superior to both coffee and tobacco in improving his concentration. He now also uses the wipes for work and before business and scientific meetings to enhance his social performance and mental acuity, and to reduce fatigue.

A 72-year old retired policeman decided to return to work as a security guard because he needed the funds to support his grand-daughter's college costs. He worked from noon to 8:30 pm and complained of weariness and fatigue which affected his activities. He said he was so tired that he could not stay awake for televised football games, even though he was an avid fan. He volunteered to try the wipes containing DIPA-1-7 and said they definitely made him more vigilant, especially when driving home from work. He said that turning on the car's air-conditioning so that the cool air vent was aimed at his face, together with menthol mints and the wipes, kept him alert, and that he no was no longer a threat on the roads. He had an 18.5 inch (47 cm) neckline and snored heavily at night, but polysomnography did not reveal sleep apnea episodes. He felt that by using the wipes on his orbit some coolness drained down onto his nasal membranes (via the nasolachrymal duct), and that this cooling sensation in his nose allowed him to breathe more freely and to sleep better at night. Currently, he is exercising more and trying to reduce food intake, in order to control his fatigue.

Several individuals also tried the wipes containing DIPA-1-6, DIPA-1-8, 2-6 and 2-7, and also found these compounds to be effective for enhancing performance and thinking, but the effects were considered somewhat less dramatic, or with some residual sting. Of these analogs, DIPA-1-8 was judged to be the best alternative to DIPA-1-7 for cognitive enhancement. In is possible, with the appropriate formulation, all of these analogs might be used as alternatives. In summary, the surprising observation made here was that use of these compounds, and in particular DIPA-1-7, can enhance skills requiring hand-eye coordination (e.g., in snooker) and concentration (e.g., in games of chance such as poker).

Case Study 2

A 48-year old female account executive was a busy professional at a large financial institution. Her husband was a successful architect. She had two teenage children and she was constantly short of time to do her chores. At the end of the day, she was frequently physically and mentally exhausted and would fall asleep early after evening meals. Due to recent marital difficulties, she felt tired and weary most of the time, and her domestic and professional demeanour, in dress and etiquette, began to deteriorate. She did not suffer from any chronic physical illness, but she was rated as having "moderate fatigue" on the Brief Fatigue Inventory (BFI) after several interviews and considered "depressed" by her physician. She volunteered to use the wipes containing DIPA-1-7 and was instructed not to use more than one per day. After two days of use, she reported that the wipes improved her mood and interest in external events. She was more energetic and positive. She completed her assignments at work promptly and had better stamina, and she was more combative and assertive. The people closest to her, children and work colleagues, also remarked on her improved change in attitude and personality. She continues to use the wipes on an as-needed basis.

A 69-year old male suffered from Parkinson's disease of 12 years duration. He is on expert medical care and has taken a variety of drugs to help manage his disease over time. In the past several years, the primary drugs (e.g., Sinemet®) became less effective and he was less mobile and more housebound. In November 2009, he was implanted with electrodes for deep brain stimulation treatment and this procedure increased his mobility. Recently, however, in spite of careful adjustment of his brain stimulation parameters, his Parkinsonism has gradually returned, and he complained of constant fatigue and depressed mood. His BFI scores were in the "moderate to severe" range of fatigue levels. He volunteered to try the wipes containing DIPA-1-7 (1 mg/mL and 5 mg/mL) and was told to limit his use to one per day. The first thing that the subject noticed, after using the wipes, was that he was able to stay awake and alert in order to watch his two favourite TV shows "House" and "Hawaii Five-0" on Monday nights (from 9 to 11 pm). He said normally he would have to make an extra effort to follow the dialogue and plot of "House" but would fall asleep before Hawaii Five-0 "got going". His general activity and mood improved and he was more willing to take his dog for a walk. He went to the golf range more often to do chipping and putting, but said he was still unable to turn to swing longer clubs off the mat. His friends noticed he was in a better mood and participated more in social events. He attributes his reduced tiredness to the wipes and looks forward to its use every morning. He said his appetite had improved, he longer felt depressed, and he wanted to be more active.

A 62-year old was diagnosed with hepatitis C virus (HCV) infection 10 years ago and was treated with PEG-interferon and ribavarin but did not respond because of his genetic makeup. He retired early from his professional career and was relatively symptom-free except for mild fatigue which required a mandatory afternoon nap of at least two hours. However, six months ago, a 3 cm diameter hepatoma was detected by magnetic resonance imaging on the margin of his lower right liver lobe. He was first treated by trans-arterial chemical embolization with doxorubicin-eluting beads (TACE) and then shortly afterwards with radiofrequency ablation when it was noted that his α-feto-protein levels were elevated, suggesting that hepatoma cells may still be present after TACE. These procedures resulted in moderate to severe fatigue, as evaluated by the BFI, which remained persistent even two months after the last treatment procedure. His initial complaint of severe pain after surgery was managed by the narcotic analgesic Vicodin®, but now his main complaint is of disturbed sleep, daytime fatigue, inability to concentrate, and memory loss. He was prescribed the hypnotic Lunesta®, but this did not help his disturbed sleep, so he is now prescribed Zolpidem®, despite the increased risks of liver damage from this drug. He volunteered to try the wipes containing DIPA-1-7 (1 mg/mL and 5 mg/mL) because he was an avid reader, belonged to a book club, and wanted to keep his mind active when his mobility was physically limited by fatigue.

After using the wipes, he commented that he was more alert and he was better able to concentrate when reading. He noted that applying the wipes to a wider surface, especially on the skin of the cheekbones and orbit, enhanced the desired sensory effect. (The delivery of the sensory agent to the neuronal receptive field is enlarged.) He noted that he had finished reading Kurt Vonnegut's biography but was discouraged from tackling the biography of Steve Jobs by Walter Issacson because of its length (more than 600 pages). After using the wipes, he finished reading the Jobs biography in three days, and was able to remember and discuss the finer details of the book with his friends. He was especially intrigued by how Jobs was treated for and responded to his cancer. He said his pain from surgery was not improved by use of the medicated wipes, and he still had aches in his joints, but his mood and his ability to carry out daily activities were improved. He noted that the exceptionally long duration of action of the active ingredient in the wipes may be of use in treatment of other chronic illnesses such narcolepsy, neurotic and major depressions, and as an adjunct in managing Alzheimer's disease. He continues to use the wipes on an as-needed basis.

These studies illustrate the potential benefits of the medicated wipes, especially those containing DIPA-1-7, for countering the tiredness and fatigue of chronic illness.

Case Study 3

In another series of studies, a towelette was used for delivery instead of a cotton wipe. The towelette consisted of a plastic wrap (weight 1.1 g), a 23 cm×26 cm towel of non-woven lace (weight 3.4 to 3.5 g) and a liquid composition (14 to 15 mL) which was automatically added to and sealed off in the wrapper. Automated machinery for producing towelettes are well-known to the art. Here, the towelettes were produced by Kank Factor, LLC, San Francisco (721 Commercial Street, San Francisco Calif. 94108, www.3LWipes.com). These towelettes were then further treated to form either embodiments for practicing the present invention or as placebo controls, as follows. Distilled water (as placebo controls) or DIPA-1-7 dissolved in distilled water (at a concentration of 1 to 5 mg/mL) was incorporated into the towelette. The volume per self-application depended on the application site, but was about 0.3 mL to 0.5 mL for the face and brow, but could be higher if wiping of the torso was also included.

The towelettes were stored in a refrigerator but then stored at room temperature for at least 1 hour before use. Effective sterilization of the towelette could be obtained by placement in a microwave oven for 1 min [Tanaka, Y. et al. Warming and sterilizing towels by microwave irradiation. Yonago Acta Medica 41: 83-88, 1998]. Subjects were instructed to hold the towelette with both hands, and bring the towelette against the face, like how one would use a small wet face towel, and to keep the eyes closed. The skin of the face is moistened and medicated by this procedure. Once the subject has learned what to expect, the subject can adjust the dosage (e.g., by dabbing), as needed, to achieve the desired anti-fatigue/anti-heat effects. After one or two trials, individuals quickly learn how to apply the sensory agent without any risks of discomfort.

During an "Indian Summer" heat wave in the San Francisco Bay Area, the outside temperature was 30 to 33° C. with a cloudless sky and an intense bright sun. The towelette, described above, was used as a substrate to deliver DIPA-1-7 to the skin of the chest and armpits of several individuals who complained vigorously about heat stress and discomfort. Comfortable cooling was noted for more than 3.5 hours with decreased sweating. These Individuals were able to work normally in the heat in an office environment without need for additional cooling.

A 70-year old from Northern California went on a 7-day golf vacation to Las Vegas in September. He played at least one round of golf each day and sometimes two. He did not wear a hat or use sunscreen. On the third day of vacation, the subject showed the classic signs and symptoms of sunburn: redness and flushing of the facial skin, a sense of persistent warmth, pain, and tenderness of the face, a mild degree of swelling around the eyes, and a throbbing headache. He volunteered to try a cream containing 1% wt/vol DIPA-1-8 and wiped about 0.5 mL of the cream over his cheeks and cheekbone. Surprisingly, he noted an immediate relief of skin discomfort which lasted for at least four hours. His headache was gone, and he said his face felt "comfortable and normal". He used the cream on an "as needed" basis and also took measures to reduce his exposure to direct sunlight by wearing a wide-brimmed hat and applying copious amounts of sunscreen products. He said that the cream would be especially useful for the dry hot climates of Los Angeles, Phoenix and other parts of Arizona, and for Texas because also relieved the sense of dryness and on the face gave also a feeling of "wetness" after repeated use.

A second-year medical student in was preparing for her Boards in the summer. During hot weather, her electricity costs increased three-fold, so that she and her roommates could not afford to turn on the air-conditioning throughout the evening hours. She said that she could cope with the heat by using a wet towel around her neck, but the main adverse effect of heat was disturbance of mental concentration for studying and the difficulty in getting comfortable sleep. She agreed to try the towellette containing DIPA-1-7 and found that it gave her prolonged and refreshing cooling sensations of her face and body. She remarked that her skin felt fresh and cool and she was better able to concentrate of her studies and to retain information. She also noted that her boyfriend said that she had a fresh and energetic look about the eyes, like Julia Roberts in her younger days, and that this look made her more attractive. She said that DIPA-1-7 may have value as a cosmetic agent to enhance beauty, as well as an aid to enhance concentration and study in an academic situation. She also noted that DIPA-1-7 might be useful in enhancing exercise tolerance, in the same way that icy collars put around the neck significantly improve athletic performance.

Case Study 4

Two scientists working in the laboratory had allergic dermatitis of the hand in response to detergents and soaps. The hands were inflamed and extremely itchy. Applications of DIPA-1-7, 20 mg/mL, with a cotton-tipped applicator immediately stopped the itch and this effect lasted for at least 2 hours, and the suppression could be renewed by repeated application. One scientist, a world-renowned dermatologist with many publications on itch, noted that the DIPA-1-7 produced an "icy-cool" feeling on the inflamed skin and he had never encountered such a compound that was so effective in stopping itch so quickly.

A pharmacologist liked to work in the garden, but the thorns from *bougainvillea* stems and rose bushes, and the hair from azalea leaves, irritated his skin and caused intense itch. He noted that the sensory discomfort on the skin could be instantly stopped by DIPA-1-6 or DIPA-1-7, applied either as a 20 mg/mL aqueous solution, or as a cream (mixed with Eucerin Moisturizing Cream). These effects could also be obtained with DIPA-1-8. He also noted that the irritation and itch caused by insect bites could be immediately stopped by these agents.

A 40-year old suffered from penile lichen sclerosus. This is an inflammatory dermatosis of the glans penis and foreskin and, in this particular case, was associated with intense pruritus and dysesthesias (burning sensations). The patient, under the supervision and care of his dermatologist, volunteered to try DIPA-1-8 on his lesion and he was supplied with various concentrations of DIPA-1-8 dissolved in distilled water. After self-experiment, he concluded that concentrations of 1 to 1.5 mg/mL of DIPA-1-8 produced significant relief, but a concentration of 2 mg/mL of DIPA-1-8 was too cold and uncomfortable. The solutions were applied with cotton-tipped applicators or gauze wipes. The advantage of using DIPA formulations for genital skin is water solubility. This minimizes the need for excipients and the likelihood of further irritation. The subject suggested that an aerosolized spray may also be a convenient method of drug delivery.

These studies illustrate the anti-nociceptive properties of DIPA-1-7 and DIPA-1-8, especially on itching. DIPA-1-8 had a longer duration of action than DIPA-1-7, and may be the preferred agent for dermatological applications.

Case Study 5

A 66-year old woman had occasional bouts of hot flushes/night sweats of about 1 episode every two weeks. She was on hormone replacement therapy (HRT) (estradiol 1 mg and medroxyprogesterone 2.5 g, once per day), but decided to stop HRT after two of her friends had breast cancer and one had uterine cancer. Her episodes of night sweats increased to about once every other day, and she and her husband were frustrated because it was necessary to change the bed sheets frequently. She agreed to try a lotion containing 1% of DIPA-1-6. This lotion was applied on the skin at the base of her neck and on the centre of her chest before going to sleep at night. If she woke up at night, the application was repeated. She said the lotion felt cool, but was not uncomfortable. No episodes of night sweats were observed for three weeks. Further discussion with her physician convinced her to return to HRT and she has not experienced night sweats for at least the past 9 months.

Case Study 6

Three subjects decided to systemically compare DIPA-1-6, DIPA-1-7, DIPA-1-8, and DIPA-1-9 for their sensory effects on the ocular surface. Each compound was prepared at 1 mg/mL in distilled water. A cotton tipped applicator of a specific size (Puritan 803-PCL) consisting of a 55 to 75 mg ball of cotton wound around the tip of a three inch polystyrene rod was dipped into the solution. The tip was then applied, with the eyelids closed, to the lower aspect of the upper eyelid, onto the eyelashes, with two lateral to medial wiping motions. The subjects were then instructed to blink. By blinking, the solution is then evenly distributed over the pre-corneal film. This "swab" delivery method off-loaded a total of ~35 μL of liquid onto the surface of both eyes. DIPA-1-6 caused significant stinging and discomfort and was therefore not further studied. DIPA-1-7 and DIPA-1-8 produced strong and refreshing cooling, which counteracted eye irritation, and increased cognitive functions. For example, subjects felt they could focus on distant objects and enjoy the view. They felt mentally alert and refreshed. But, with both DIPA-1-7 and DIPA-1-8, there was a small residue left on the eyelid; subsequently using a towel to wash the face can cause eye irritation. Surprisingly, DIPA-1-9 did not produce any eye irritation when wiped over the eyelid, nor did it leave a residue. It also produced refreshing cooling, but not with the same intensity as DIPA-1-7 or DIPA-1-8. On the other hand, DIPA-1-9 has ideal properties for the treatment of ocular discomfort, e.g., discomfort caused by eye strain; eye fatigue; eye surgery; an airborne irritant or pollutant that interacts with the eye surface; extended wear of contact lenses; excessive exposure to the sun; conjunctivitis; or the dry eyes syndrome.

Case Study 7

A 2-year old female West Highland Terrier developed, during the summer, an itching condition which led to continued scratching of the ears and underbelly. The veterinarian diagnosed the behavior as canine atopy and prescribed oral antihistamines. These drugs did not control the progression of the itching and patches of raw skin, with hair loss, occurred at the base of the tail and on the hind limbs. A topical anti-inflammatory steroid, triamcinolone, provided limited success and the dog still looked miserable. Surprisingly, application of DIPA-1-7 cream (1% wt/vol) to the inflamed skin sites immediately reduced scratching and the skin sites begin to heal. It was clear from the dog's behavior that the itching was reduced in severity. Further curtailment of the dog's access to the outdoors and control of possible exposure to fleas and dust mites resulted in a successful control of the dog's skin disorder.

Case Study 8

The eyes are extremely sensitive to injury and the symptoms of injury include blurring of vision, itching, irritation, burning sensations, sensations of a foreign object, and pain. The ability of DIPA-1-9 to produce prolonged cooling without residual discomfort suggested that it might be useful in the treatment of the "dry eyes syndrome", a widely prevalent condition in the general population. Prof KC Yoon, the leading ophthalmologist for "dry eyes syndrome" [DES] in Korea conducted a clinical trial of DIPA-1-9 in normal and in patients diagnosed with DES. For this DIPA-1-9 study, there were 12 normal subjects and 15 DES patients. The characteristics of the study population are shown in Table 11. The trial was approved by the Institutional Review Board of Chonnam University, Gwangyu, Korea.

Ten drops of DIPA-1-9, 2 mg/mL in saline, was placed on a cotton gauze pad and wiped onto the upper eyelids of subjects, with the eyes closed. Change in symptoms of ocular surface cooling sensation were obtained by questionnaire using a visual analog scale scores (0 to 10) at every 5 min interval. The tear film break-up time (BUT) was measured at 10 min intervals, and the Schirmer test I (without anesthesia) was measured at 20 min intervals, the ocular surface epithelial damage score (keratoepitheliopathy) was recorded using the National Eye Institute (NEI) system. Corneal sensitivity to a microfilament was measured using Cochet-Bonnet esthesiometry. The characteristics of the test subjects are shown the Table 11. After application the onset of coolness reached a peak score of 6 within 5 min and steadily decreased thereafter. The average duration of coolness was 47 min and there was no difference between the two subject groups. The tear BUT and the Schirmer test 1 scores were significantly improved in the DES group, but there were no significant changes in the scores of "normal" subjects. The effects on BUT and Schirmer lasted for ~30 min after application of DIPAP-1-9. There were no changes in corneal sensitivity to mechanical stimulation.

TABLE 11

Characteristics of subjects exposed to DIPA-1-9, 2 mg/mL, in eye wipes.

| | Normal | Dry eye | P-value |
| --- | --- | --- | --- |
| Sex (M/F) | 5/7 | 8/7 | |
| Age | 26.67 ± 2.99 | 27.80 ± 3.45 | |
| BUT(sec) | 9.75 ± 1.54 | 3.80 ± 1.82 | <0.001 |
| Schirmer I test(mm) | 14.10 ± 3.52 | 7.33 ± 2.97 | 0.003 |
| Keratoepitheliopathy | 0.25 ± 0.62 | 1.33 ± 1.11 | 0.004 |
| Corneal sensitivity (mm) | 59.17 ± 2.89 | 58.67 ± 3.52 | 0.829 |

In the opinion of Prof Yoon the symptomatic relief seen in the DES patients receiving DIPA-1-9 is quantitatively better than the results seen in his laboratory with approved drugs for DES; namely, cyclosporine 0.5% and diquasol, a P2Y2 agonist. Further studies, with a larger test group and a 4-week regimen of treatment are in progress and the results will be publicly communicated.

REFERENCES

A number of publications are cited herein in order to more fully describe and disclose the discovery and the state of the art to which the discovery pertains. Each of these publications is incorporated herein by reference in its entirety into the present disclosure

The invention claimed is:

1. A therapeutic method for the treatment of skin dyesthesia dysesthesia in a subject in need of treatment thereof, comprising:
topically applying a liquid or semi-liquid composition to keratinized tissues of the subject's skin, the composition comprising a therapeutically effective amount of one or more compounds having Formula 1

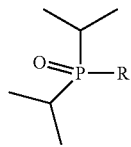

Formula 1 wherein R is n-heptyl, n-octyl or n-nonyl;
wherein the liquid or semi-liquid composition further comprises a pharmaceutically acceptable carrier, diluent, or excipient; and
wherein the liquid or semi-liquid composition, following topical application, penetrates the keratinized tissues of the subject's skin.

2. The method as in claim 1 wherein the liquid or semi-liquid composition has from about 0.05 to 2% by weight of the Formula 1 compound.

3. The method as in claim 1 wherein the Formula 1 compound is 1-diisopropyl-phosphinoyl-heptane (DIPA-1-7), 1-diisopropyl-phosphinoyl-octane (DIPA-1-8), and/or 1-diisopropyl-phosphinoyl-nonane (DIPA-1-9) and the therapeutically effective amount is from 1-20 mg/ml.

* * * * *

UNITED STATES PATENT AND TRADEMARK OFFICE
CERTIFICATE OF CORRECTION

PATENT NO. : 10,195,217 B2
APPLICATION NO. : 14/544355
DATED : February 5, 2019
INVENTOR(S) : Edward T. Wei Page 1 of 1

It is certified that error appears in the above-identified patent and that said Letters Patent is hereby corrected as shown below:

In the Claims

In Column 48, Lines 61-62 of Claim 1 "dyes-thesia" should be deleted.

Signed and Sealed this
Tenth Day of November, 2020

Andrei Iancu
*Director of the United States Patent and Trademark Office*